United States Patent [19]

Waterfield et al.

[11] Patent Number: 4,933,294

[45] Date of Patent: Jun. 12, 1990

[54] METHOD OF DETECTING TRUNCATED EPIDERMAL GROWTH FACTOR RECEPTORS

[75] Inventors: Michael D. Waterfield, London, England; J. Schlessinger, Rehovot, Israel; Axel Ullrich, South San Francisco, Calif.

[73] Assignees: ICRF Patents Limited, London, England; Research & Development Co., Ltd. Yeda, Rehovot, Israel; Genentech, Inc., South San Francisco, Calif.

[21] Appl. No.: 783,951

[22] PCT Filed: Jan. 30, 1985

[86] PCT No.: PCT/GB85/00045

§ 371 Date: Dec. 2, 1985

§ 102(e) Date: Dec. 2, 1985

[87] PCT Pub. No.: WO85/03357

PCT Pub. Date: Aug. 1, 1985

[30] Foreign Application Priority Data

Jan. 30, 1984 [GB] United Kingdom ................ 8402379
Jan. 9, 1985 [GB] United Kingdom ................ 8500538

[51] Int. Cl.$^5$ .................. G01N 33/53; G01N 33/566; G01N 33/543; C12Q 1/48

[52] U.S. Cl. ........................................ 436/501; 435/4; 435/7; 435/15; 436/503; 436/518; 436/813; 436/815; 436/817

[58] Field of Search ................. 435/7, 15, 4; 436/501, 436/503, 504, 518, 804, 813, 817, 815

[56] References Cited

PUBLICATIONS

Lin, C., et al., Science, 224:843–848 (1984).
Xu, Y. H., et al., Nature, 309:806–810 (1984).
Ullrich, A., et al., Nature, 309:418–425 (1984).
Merlino, G., et al., Science, 224:417–419 (1984).

*Primary Examiner*—Robert J. Warden
*Assistant Examiner*—Jack Spiegel
*Attorney, Agent, or Firm*—Cushman, Darby & Cushman

[57] ABSTRACT

Neoplastic and other diseases can be diagnosed by assaying a human test sample e.g. body fluid, tissue or cultured tumor explant cells, for structurally altered or abnormally expressed growth factor receptors or for the RNA transcripts of genes which encode them. For example, the assay can be for truncated EGF receptor having at least a portion of its mature amino terminus deleted. Antibodies, capable of binding a predetermined amino acid sequence within the EGF receptor, are also useful in diagnosis and therapy as are conjugates of an immunogenic polymer bound to a polypeptide fragment of EGF receptor. DNA and RNA encoding EGF receptor or fragments thereof are also described.

8 Claims, 12 Drawing Sheets

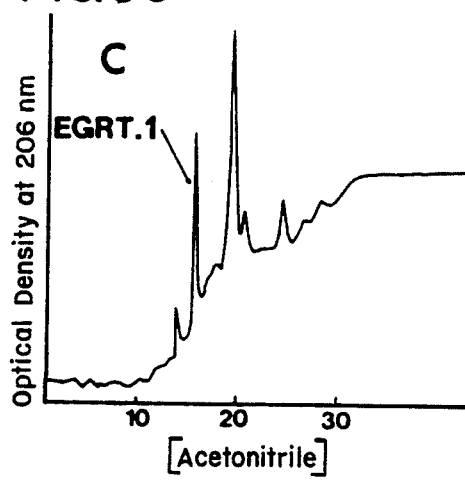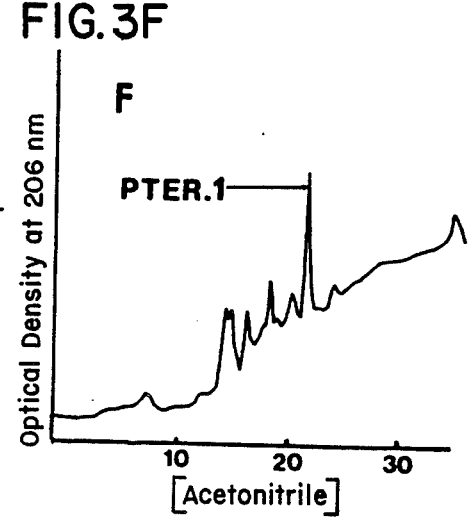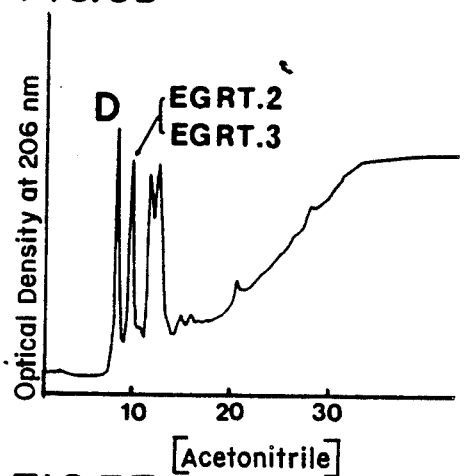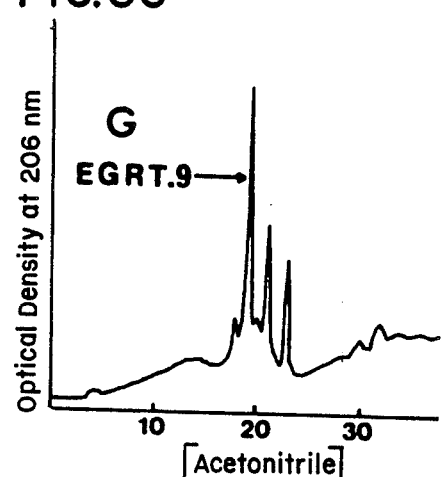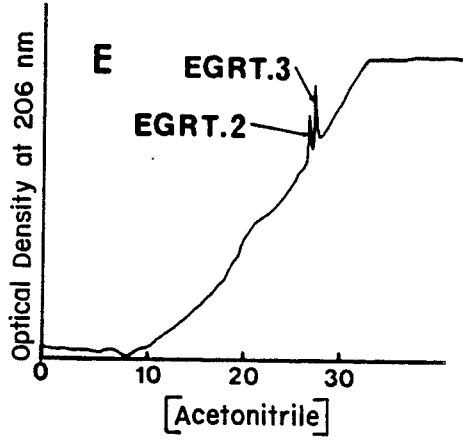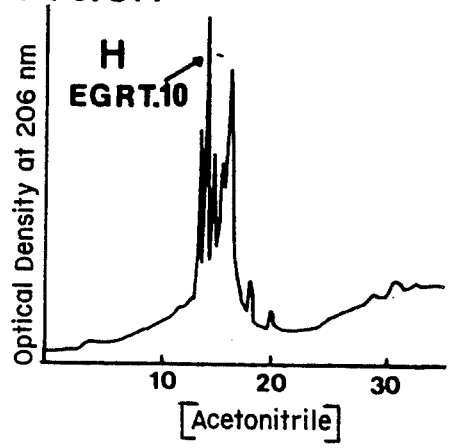

```
Src    1   MGSSKSKPKDPSQRRHSLEPPDSTHHGGFPASQTPDETARPDAHRNPSRS

Src   51   FGTVATEPKLFWGFNTSDTVTSPQRAGALAGGVTTFVALYDYESWTETDL

Src  101   SFKKGERLQIVNNTEGDWWLAHSLTTGQTGYIPSNYVAPSDSIQAEEWYF
                                                MKCAHFIDGPHCVKA

Src  151   GKITRRESERLLLNPENPRGTFLVRKSETAKGAYCLSVSDFDNAKGPNVK
ErB-B   1  CPAGVLGENDTLVRKYADANAVCQLCHPNCTRGCKGPGLEGCPNGSKTPS

Src  201   HYKIYKLYSGGFYITSRTQFGSLQQLVAYYSKHADGLCHRLANVCPTSKP
ErB-B  66  IARGVVGGLLCLVVGLGIGLYLRRRHIVRKRTLRRLLQERELVEPLT-P
                                                 ELVEPLT-P

Src  251   QTQGLAKDAWEIPRESLRLEAK-LGQGCFGEVWMGTWN--D---TTRVAI
ErB-B 115  SGEAPNQAHLRILKETEFKKVKVLGSGAFGTIYKGLWIPEGEKVKIPVAI
           SGEAPNQALLR        WVLGSGAFGTVYKGLWIPEGEK

Src  295   KTLKPGTMSPEA---FLQEAQVMKKLRHEKLVQLYAVVSEEPIYIVIEYM
ErB-B 165  KELREAT-SPKANKEILDEAYVMASVDNPHVCRLLGICLTSTVQLITQLM

Src  342   SKGSLLDFLKGEMGKYLRLPQ-LVDMAAQIASGMAYVE-RMNYVHRDLRA
ErB-B 214  PYGCLLDY-IRE-HKDNIGSQYLLNWCVQIAKGMNYLEERR-LVHRDL-A
```

FIG. 5

```
Src  390  A-NILVGENLVCKVADFGLARLIE-D-NEYTARQGAKFPIKWTAPEAALY
Erb-B 268 ARNVLVKTPQHVKITDFGLAKLLGADEKEYHAEGG-KVPIKWMALESILH

Src  437  GRFTIKSDVWSFGILLTELTTKGRVPYPGMVNREVLDQVERGYRMPCPPE
Erb-B 389 RIYTHQSDVWSYGVTVWELMTFGSKPYDGIPASEISSVLEKGERLPQPPI

Src  487  CPESLHDLMCQCWRKDPEERPTFKYLQAQLLPACVLEVAE
Erb-B 359 CTIDVYMIMVKCWMIDADSRPKFRELIAEFSKMARDPPRRYLVIQGDERMH

Erb-B 409 LPSPTDSKFYRTLMEEEDMEDIVDADEYLVPHQGFFNSPSTSRTPLLSSL
                              WGDVVDADEYLIPQQGFF

Erb-B 459 SATSNNSATNCIDRNGQGHPVREDSFVQRYSSDPTGNFLEESIDDGFLPA

Erb-B 509 PEYVNQLMPKKPSTAMVQNQIYNFISLTAISKLPMDSRYQNSHSTAVDNP

Erb-B 559 EYLNTNQSPLAKTVFESSPYWIQSGNHQINLDNPDYQQDFLPTSCS
                                   GSHQISLDNPDYQQDFF
```

FIG. 5 – cont.

FIG. 7
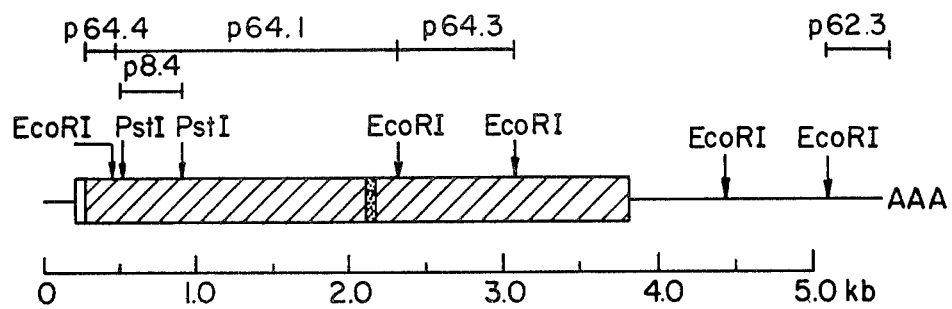
FIG. 8

METHOD OF DETECTING TRUNCATED EPIDERMAL GROWTH FACTOR RECEPTORS

This invention relates to new polypeptides of interest in the detection of abnormalities in mammalian cell growth and in the control of mammalian cell growth.

Regulation of the proliferation of cells in culture can be influenced by a number of mitogens including a series of polypeptide growth factors which, acting alone or synergistically with other mitogens, can induce DNA synthesis and proliferation of specific target cells. (For recent reviews see ref. 1). Epidermal growth factor (EGF) and platelet derived growth factor (PDGF) are probably the best characterised growth factors, however the precise function of these polypeptides in vivo is unclear. EGF may have a role in cell proliferation and differentiation since it will induce early eyelid opening and incisor development in new born mice (2); PDGF on the other hand, which is released from platelets during blood clot formation at wound sites, may have a role in repair processes (3). These and other growth factors in vitro can trigger a variety of morphological and biochemical changes that resemble those characteristic of transformed cells, and have also been implicated in the abnormal regulation of proliferation shown by transformed and tumour-derived cell lines (reviewed in (4,5)). Thus it has been suggested that transformed cells may both synthesise and respond to growth factors and consequently proliferate independently through 'autocrine' secretion (6). Direct support for such an autocrine role for aberrantly expressed growth factors in the control of abnormal cell proliferation came recently from the discovery that the putative transforming protein ($p28^{sis}$) of simian sarcoma virus (SSV) is structurally related to the growth factor PDGF (7-9) and can also function like PDGF as a growth factor for cells in culture (10). Other growth factors produced by transformed cells such as insulin-like growth factor (IGF) (11,12), fibroblast derived growth factor (13,14) and the transforming growth factors (TGFs) (15-20), may also act as autocrine regulators of proliferation. Besides the specificity mediated by regulation of the production of growth factors, cellular specificity could also be controlled at several other levels—the most obvious being by binding of ligand to specific receptors present only on target cells. In addition the binding of one growth factor to its specific receptor can also alter the affinity of another growth factor for its receptor (e.g., PDGF and the EGF receptor (21,22)). Conversely two growth factors may, as appears to be the case with αTGFs and EGF, bind to the same receptor (23,24).

It is clear that binding of different growth factors to their specific receptors can induce a cascade of biochemical events including rapid changes in ion movements and intracellular pH, stimulation of tyrosine specific protein kinases and several other changes which can culminate in DNA synthesis and proliferation of certain target cells (1,4-6). It seems likely that at least in the case of the EGF receptor the primary function of EGF may be to induce cross-linking or conformational changes of receptors, and that following such an activation step, all the 'information' necessary for triggering a proliferative response may reside in the receptor itself (see reviews in reference 1). One known function intrinsic to the EGF receptor is its ability to prophorylate tyrosine residues (25-28), a property shared with 5 of the putative transforming proteins of the family of retrovirus whose oncogenes are related to src but not by 2 others, the proteins encoded by mos and erb-B (29). At present this tyrosine kinase activity provides the only functional activity associated with the oncogenes of this subset of retroviruses. None of this family of oncogenes has heretofore been identified as having a cellular homologue that functions as a growth factor receptor.

We have determined the amino acid sequence analysis of 6 distinct peptides from human EGF receptors isolated by monoclonal immunoaffinity purification from A431 cells and placents, and show that 74 out of 83 of the residues sequenced are identical to those of the transforming protein encoded by the v-erb-B oncogene of avian erythroblastosis virus (AEV) (30). Subsequent work (Ullrich et al (76)) confirms the homology between the v-erb-B oncogene and the human EGF receptor and describes the remaining homologous sequences which show that AEV has acquired cellular sequences encoding only a portion of the avian EGF receptor. Several lines of evidence suggest that the v-erb-B oncogene encodes only the transmembrane region of the EGF receptor, the domain associated with the tyrosine kinase activity and a short region of the receptor not including the EGF binding site. We believe that the src related subset of oncogenes, which includes v-erb-B, are derived from cellular sequences which encode growth factor receptors and produce transformation through expression of uncontrolled receptor functions.

We have discovered that the v-erb-B oncogene contains significant homology with the human EGF receptor. We conclude that structural alterations of the human EGF receptor and its gene or alterations in transcription and expression of the human EGF receptor gene are capable of being integrally involved in tumourgenesis in humans and that accordingly it is now apparent that assays and therapies involving the human EGF receptor are warranted as a measure of or for the control of tumours in humans.

Such assays in humans can involve detection in body fluids or tissues etc., of structurally altered or abnormally expressed growth factor receptors and the mRNA transcripts and genes which encode them. Examples of such structural alteration are truncation of the receptor at at least the N-terminus. Therapy may involve the use of reagents e.g. antibodies that recognise the abnormal receptors. The assays can be carried out at protein level, RNA level or DNA level. Initially, our knowledge of part of the amino acid sequence of the receptor allowed us to generate reagents of value in diagnosis and our later determination of the full amino acid sequence of the receptor has extended our knowledge in this area.

Examples of such reagents are synthetic polypeptides I of the sequence or including the sequence

|    | | |
|---|---|---|
|    | ELVEPLTPSGEAPNQALLR | Ia |
| or | VLGSGAFGTVYK | Ib |
| or | GLWIPEGEK | Ic |
| or | YLVIQGDER | Id |
| or | DVVDADEYLIPQQGFF | Ie |
| or | GSHQISLDNPDYQQDFF | If |

Polypeptides including the sequences Ia-If are examples of truncations of EGF receptors and when we refer below to polypeptides I we mean to refer not only to the polypeptides including the sequences Ia to If above but also to other EGF receptor fragments truncated at at least the N terminus.

By "synthetic" we mean chemically synthesised, e.g. by solid phase techniques, or biochemically synthesised by cells that do not, in their natural state, biosynthesis polypeptides I as defined above.

In the Specification, we are using the Internationally recognised abbreviations for the naturally occurring L-amino acids as set out in Atlas of Protein Sequences (1972).

Specifically, the following abbreviations are used:

| | |
|---|---|
| A = Alanine | L = Leucine |
| | M = Methionine |
| C = Cysteine | N = Asparagine |
| D = Aspartic acid | P = Proline |
| E = Glutamic acid | Q = Glutamine |
| F = Phenyl alanine | R = Arginine |
| G = Glycine | S = Serine |
| H = Histidine | T = Threonine |
| I = Isoleucine | V = Valine |
| K = Lysine | Y = Tyrosine |
| | W = Tryptophane |

Polypeptides I are of interest in the diagnosis of abnormalities involving the EGF receptor in neoplastic and other diseases. For this purpose, interest centers not only on the polypeptides I themselves but also on their analogues, e.g. phosphorylated analogues and analogues in which a group such as a lipid group is introduced into the molecule to facilitate drug targetting.

Polypeptides I are also of interest in inhibiting the activity of normal or abnormal EGF receptors expressed in cancers cells. For this purpose, interest centers not only on the polypeptides I but also on their antigenic analogues in which variation may occur in the amino acid sequence but where the analogue still provokes substantially the same antigenic response in a host.

Polypeptides I are also of interest in that they provide a basis for the construction of synthetic oligonucleotides II which encode polypeptides I, such oligonucleotides II being of value in diagnosing abnormal receptor expression. The synthetic oligonucleotides II are also of value in the identification of cDNA clones containing the nucleotide sequence of II and extensions thereof, the extended oligonucleotides themselves being of particular value in diagnosis of abnormal receptors in disease. These synthetic oligonucleotides II form a further aspect of the present invention.

According to a further feature of the invention, we provide a process for the production of a synthetic polypeptide of formula I as defined above comprising chemically synthesising, by methods known per se, a polypeptide of formula I as defined above in which the terminal amino group and the terminal carboxy group and any intermediate amino or carboxy groups are protected with a protecting group conventionally used in peptide synthesis and then removing the protecting group. In this synthesis, the polypeptides of the invention may be synthesised for example by solid phase methods according to the Merrifield technique building up the desired amino acid sequences either one amino acid unit at a time or using blocks of several amino acid units in each step of the synthesis. In accordance with conventional methods for the synthesis of peptides, the reactive terminal amino and carboxy groups are protected as are any potentially reactive groups located at intermediate positions in the peptide chain so that reaction occurs only at the desired growth point and, in a final step, the various protecting groups can then be removed by conventional methods.

According to a still further feature of the invention, we provide a pharmaceutical preparation comprising a synthetic polypeptide I as defined above in association with a pharmaceutical diluent or carrier.

According to a still further feature of the invention, we provide a method of preparing a monoclonal antibody which comprises injecting a mouse with a synthetic polypeptide I as defined above, hybridising spleen cells of the injected mouse with myloma cells to form a hybridoma and recovering the monoclonal antibody expressed by the hybridoma.

According to a still further feature of the invention, we provide a monoclonal antibody obtained from the hybridoma described above and a pharmaceutical preparation comprising such a monoclonal antibody in association with a pharmaceutical diluent or carrier.

DESCRIPTION OF THE DRAWINGS

FIG. 5 shows the relationship between the amino acid sequence of the EGF receptor peptides and the predicted amino acid sequences of the putative transforming proteins of v-src and v-erb-B.

FIG. 7 shows the nucleic acid probes used to analyse the receptor gene and its expression at the RNA level.

FIG. 8 shows an analysis of mRNA expression in normal and tumour tissue.

PURIFICATION OF THE EGF RECEPTOR

Figure 1A:
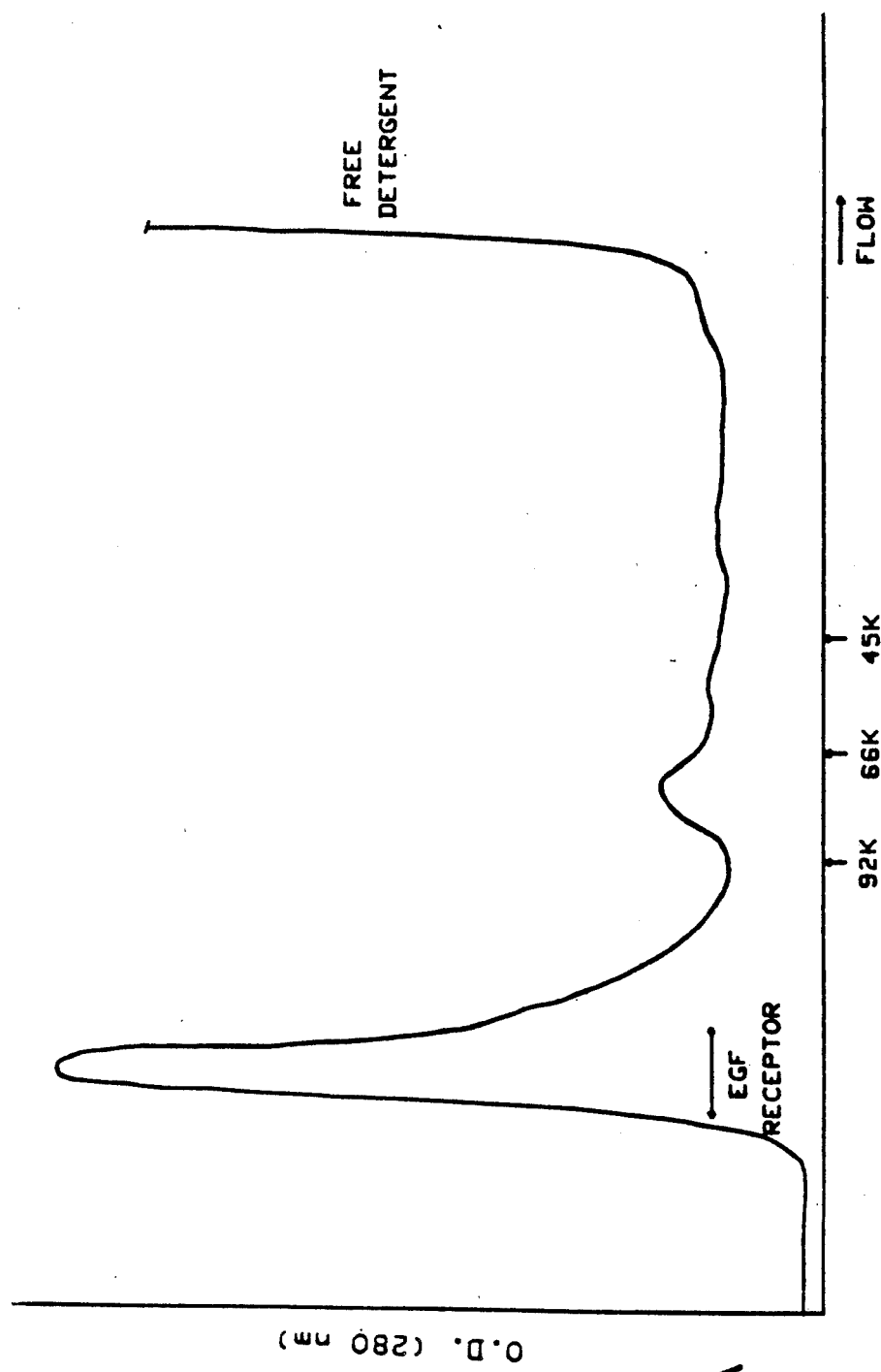
FIG. 1 illustrates the immunopurification of EGF receptor from A431 cells and human placenta.
Figure 1B:
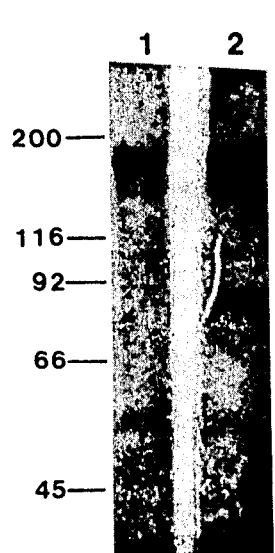
Figure 1C:
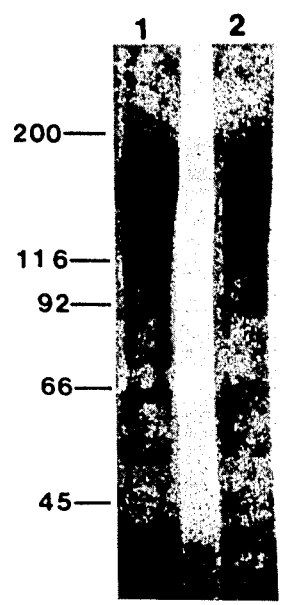
Figure 1D:
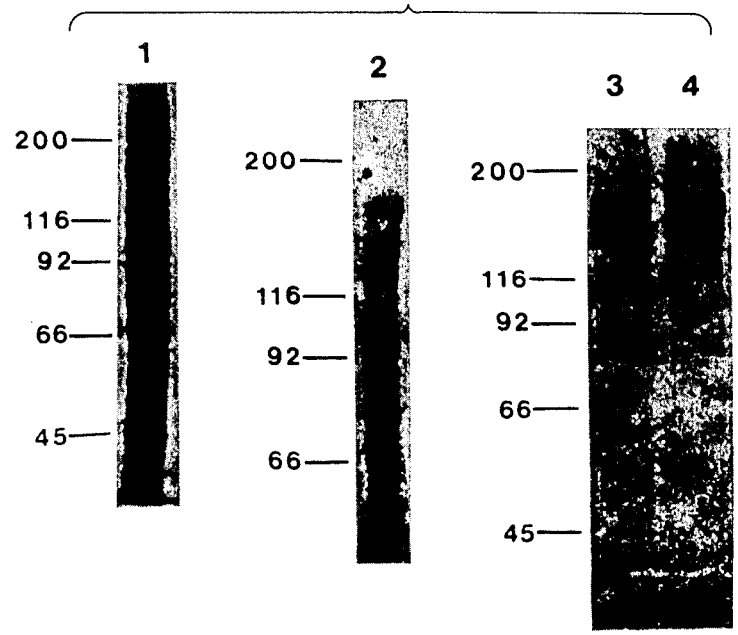

EGF receptors can be detected in a variety of cells either by measurement of EGF binding (reviewed in 31), by cross-linking of labelled EGF to its receptor (reviewed in 32), or through the use of monoclonal antibodies (33–38). In this study the receptor has been purified from two sources: the human epidermoid carcinoma cell line A431 which expresses about 50-fold more receptors than the majority of other cells (39,40) and human placenta (41) which is a readily available normal tissue. The recent isolation of monoclonal antibodies which recognise the human EGF receptor (34,38) has made it possible to use immunoaffinity chromatography for receptor purification. Here we compare by peptide mapping EGF receptor protein purified by either immunoaffinity or EGF affinity chromatography (26) and also compare the structures of the A431 and placental receptors.

A radioimmunoassay (RIA) which uses a monoclonal antibody (R1) has been used to quantitate various preparative techniques (42). Receptors from A431 cells and placenta were both found to be unstable in detergent-solubilized whole cell or tissue lysates, perhaps as a result of the release of proteases from the cellular lysosomal compartment. This problem was overcome for placenta by the preparation of syncytiotrophoblast microvillus plasma membranes and as a result a 50-fold purification with a 30% yield of receptor was achieved. Unfortunately, with A431 cells the yield of receptor in plasma membrane preparations was impractically low. However quantitative studies with the receptor RIA showed that rapid adjustment of the lysate pH to 8.5 followed by fast immunoaffinity chromatography of whole cell lysates minimised the effects of the proteases.

Placental membranes were solubilized and glycoproteins separated by wheat gearm agglutinin (WGA) affinity chromatography to achieve a partial purification. EGF receptor was then purified from the placental glycoprotein fraction or from A431 cell lysates by immunoaffinity chromatography on either monoclonal antibodies R1 (34) or 29-1 (38) immobilised on agarose or Sepharose respectively. Non-specifically bound protein was removed by washing the columns with a high salt buffer and the receptor was eluted at pH 3. The receptors were further purified either on preparative SDS polyacrylamide gels or by gel permeation HPLC in guanidine solutions (43). Details of the methods used and the yields of purified receptors are given in the legends to FIG. 1. Since the EGF binding and protein kinase activity were partially destroyed during purification, receptor was also purified by EGF affinity chromatography (26). Comparator HPLC tryptic peptide maps were then carried out to establish the purity and structural similarity of receptor prepared by immunoaffinity chromatography from A431 cells and placental tissue. The peptide maps of the receptors (see FIG. 2) showed that the elution profiles of the receptor tryptic peptides were very similar whether receptor was purified by EGF affinity or by immunoaffinity chromatography, from A431 cells or from placental tissue.

AMINO ACID SEQUENCE DETERMINATION

Receptor was purified by immunoaffinity chromatography followed by either preparative SDS gel electrophoresis or by gel permeation HPLC in guanidine (43) after reduction and alkylation (44) to cleave disulphide bonds (see FIG. 1). Purified receptor was then digested with trypsin or cyanogen bromide (see FIGS. 2 and 3) and peptides were separated by preparative reverse phase HPLC (45.46) (FIG. 3). Amino acid sequences were determined with a gas phase sequencer constructed and operated as described by Hewick et al., (47) using the analytical techniques for the quantitation of PTH amino acids described by Waterfield et al., (48). The quantitative data for analysis of 6 peptides are shown in FIG. 4.

SEQUENCE COMPARISON WITH v-erb-B TRANSFORMING PROTEIN

The amino acid sequences of 14 different peptides from the human EGF receptor, 3 from placenta and 11 from A431 cells, were compared with sequences in an oncogene sequence data base (set up at ICRF using published sequences) by the rapid search techniques of Wilbur and Lipmann (49). A remarkable identity was found between the sequences of 6 of these peptides and regions of the predicted sequence of the putative transforming protein v-erb-B of the AEV-H (30). Of the 83 amino acid residues from these 6 sequenced peptides, 74 residues were identical and 4 showed conservative substitutions when they were aligned with the v-er-B encoded protein sequence, as shown in FIG. 5. Peptide 1 was located near the amino terminus of the v-erb-B protein (residues 107–125) and peptide 6 at the C-terminus (residues 583–599), with the other 4 peptides in between. It was not necessary to introduce any deletions or insertions into the sequences to optimise the alignments.

Although the full extent of the similarity between the v-erb-B protein and EGF receptor sequences is not revealed by these limited sequence studies, it is likely that the region of the v-erb-B protein from residue 107 to the C-terminus has extensive homology to the EGF receptor. The degree of identity observed is very high and since the v-erb-B sequences of AEV were presumably of avian origin (30) while the EGF receptor sequences were from the human protein, it is likely that the v-erb-B sequences were mainly acquired by AEV from those cellular sequences which encode the avian EGF receptor. This suggests that the c-erb-B locus encodes the EGF receptor in humans and birds.

The amino acid sequence of 8 of the 14 peptides purified from the EGF receptor (data not shown) could not be aligned with the predicted sequences of the v-erb-B protein. Since the polypeptide backbone of the EGF receptor glycoprotein is thought to be about 1250 amino acids (50) and the predicted v-erb-B protein is only 604 amino acids (30) the most likely explanation is that these 8 peptides are encoded by a region of c-erb-B which has not been acquired by AEV. This could have arisen by a recombination event(s) which resulted in only a part of the EGF receptor coding sequences being acquired by AEV. Although it is possible that DNA rearrangements of receptor coding sequences occur similar to those found with immunoglobulins, it is more likely that differential mRNA splicing would be involved in any such recombination events. It has been shown that avian cells contain two c-erb-B related transcripts (51) and studies of the biosynthesis of the EGF receptor in A431 cells suggest that both a normal and a truncated receptor may be synthesised (50). Alternatively 2 or more loci encoding polypeptides having very similar amino acid sequences to those of the EGF receptor exist on chromosome (vide infra). An example of two closely related putative transforming proteins with tyrosine kinase activity has been reported in studies of the avian retroviruses Rous sarcoma virus (RSV) and Y63 (52). The predicted amino acid sequences of the proteins encoded by the src and yes oncogenes were shown to be 82% homologous over a region covering 436 amino acid residues (while the DNA sequences were only 31% homologous overall) and presumably the chicken genome contains both src and yes proto-oncogenes encoding separate proteins sharing extensive regions of sequence. It is not know whether human c-src and c-yes are encoded by closely linked loci. However, analysis of the human-mouse somatic cell hybrids has shown that the locus encoding the human EGF receptor is on chromosome 7 (7p13-7q22) (53–55) and that for c-erb-B is in the same region of this chromosome (7pter-7-q22) (56).

SHARED REGIONS OF SEQUENCE

Several lines of evidence suggest that the EGF receptor protein can be divided into 3 major domains; an EGF binding domain which lies external to the plasma membrane, a transmembrane domain and a cytoplasmic kinase domain having both the kinase activity and the autophosphorylation sites.

Investigations of receptor biosynthesis show that the A31 receptor is a glycoprotein of apparent molecular weight MW 175,000, having approximately 37,000 MW of oligosaccharide side chains with a polypeptide backbone of approximately 138,000 MW (about 1,250 amino acids). Limited proteolysis of the mature receptor suggests that the domain external to the plasma membrane which contains the oligosaccharide side chains and the antigenic sites for monoclonal R1 has a MW of about 115,000 (about 640 amino acids) (50). Several studies show that the EFG binding site is external to the plasma membrane (25,31,32).

The location of the tyrosine kinase enzymatic activity and the autophosphorylation sites on the cytoplasmic domain is supported by studies made using A431 and placental membrane vesicles.

These show that EGF stimulated tyrosine kinase activity directed towards artificial substrates or towards autophosphorylation sites is significantly activated only after membrane permeabilization. Furthermore, the tyrosine kinase activity can phosphorylate pp33-a protein known to be located at the cytoplasmic side of the membrane (57). In addition recent studies show that antibodies raised against synthetic peptides from pp60$^{v-}$src recognize antigenic sites on the human EGF receptor that are from regions of sequence homologous to the sequence of v-erb-B (vide infra). These sites are only accessible in permeabilized cells.

Figure 3A:
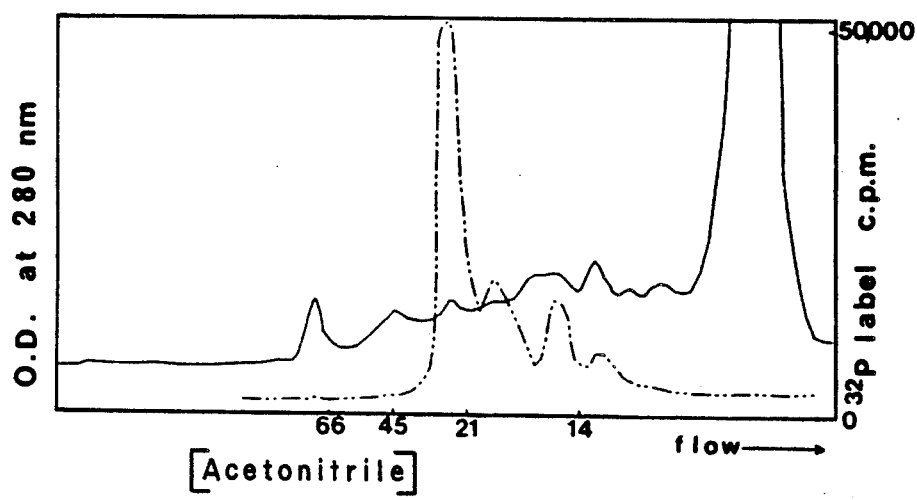
FIG. 3 shows optical density of eluates at 206 nm plotted against acetonitrile concentration produced in the purification of peptides from EGF receptor for sequence analysis.
Figure 4A:
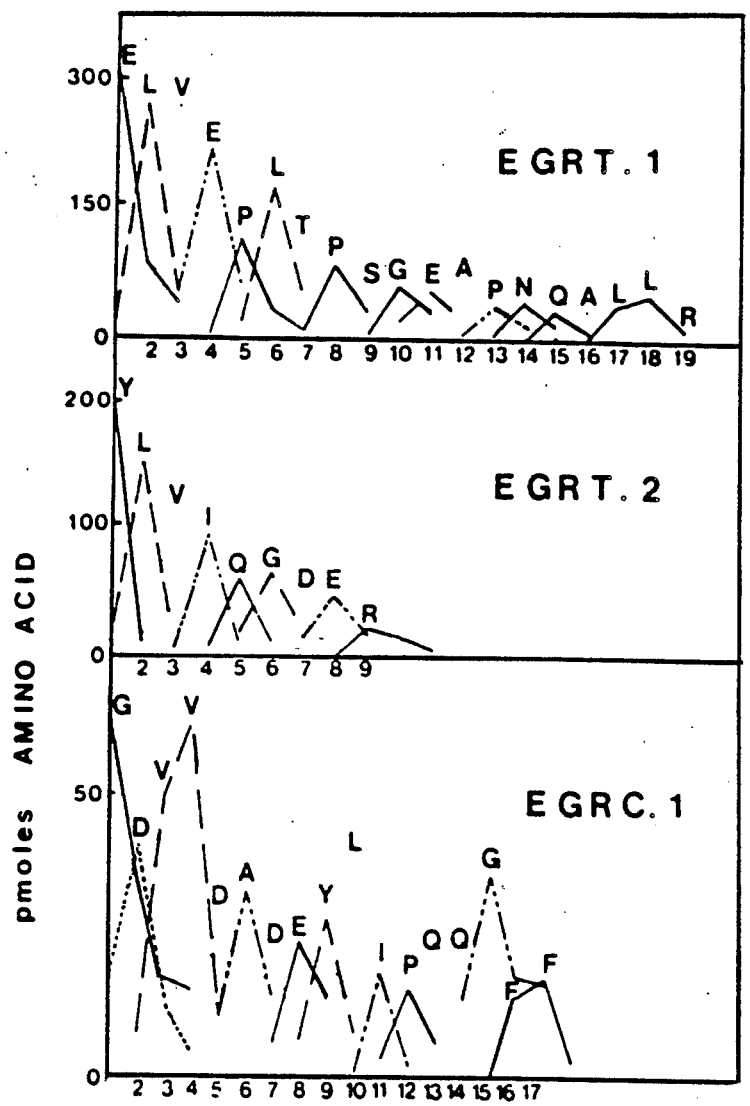
FIG. 4 shows a sequence analysis of peptides from the EGF receptor.
Figure 4B:
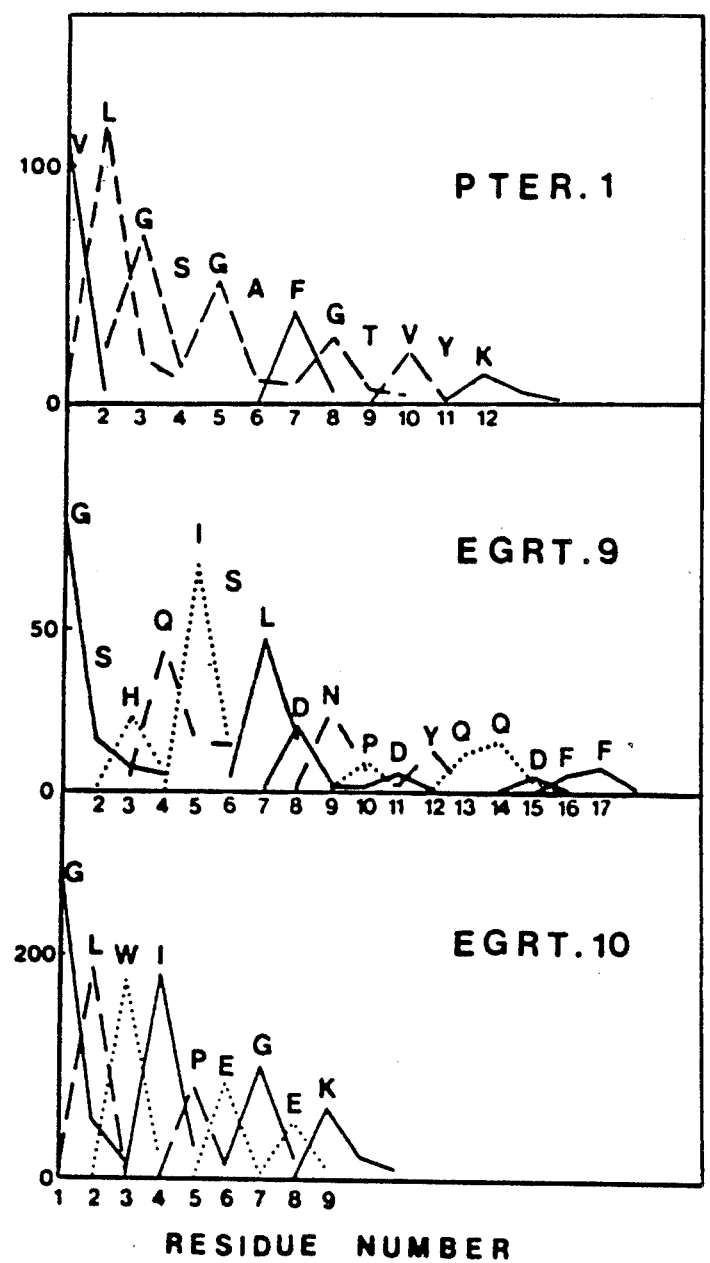

Autophosphorylation sites are located within peptide 5 (EGRC.1), a 20,000 molecular weight cyanogen bromide fragment which contains 70% of the $^{32}$P-label present in the autophosphorylated receptor (see FIG. 3A). Although the precise location of the residues phosphorylated has not been determined a concensus tyrosine phosphorylation sequence (58) was found near the amino terminus of this peptide. Therefore we believe that the tyrosine phosphorylation sites lie within the cytoplasmic domain of the EGF receptor which is contained in the sequence shared with the v-erb-B protein.

Preliminary nucleotide analysis of cDNA clones selected from an A431 cDNA library using synthetic oligonucleotide probes synthesised on the basis of the receptor amino acid sequence shows that the predicted carboxyl terminus of the EGF receptor extends 25 amino acids from an amino acid equivalent to residue 601 (see FIG. 5) of the predicted v-erb-B protein sequence (Ullrich et al., 76). This analysis when complete will show the precise size and sequence of the presumptive cytoplasmic domain of the EGF receptor. The approximate molecular weight of this domain would be 60,000 (or 550 amino acids) since that part which is external to the membrane is thought to have a molecular weight of 115,000 (see above) (50). Thus the cytoplasmic domain would be predicted to be similar in size to that region of the v-erb-B protein which is carboxy terminal to a putative transmembrane sequence (see FIG. 5 and (30)) at residues 66–88. This carboxy terminal region of v-erb-B would have a molecular weight of 56,000 and would contain 510 amino acids.

The putative transmembrane sequence of the v-erb-B protein is not preceded by a signal sequence for membrane insertion. Nevertheless, immunofluorescence studies of AEV transformed cells show that the v-erb-B protein has antigenic sites external to the plasma membrane (59). This external region probably corresponds to the 65 residue amino terminal section that precedes the putative transmembrane sequence and contains three asparagine residues which have the oligosaccharide attachment recognition sequence asn-x-ser or thr. Some or all of these residues may be glycosylated since in vitro translation studies of mRNA from AEV infected cells show that post translational processing of nascent polypeptides occurs in the presence of membrane vesicles (59,60).

Together these studies suggest that the predicted v-erb-B transforming protein closely resembles the transmembrane region of the EGF receptor and the domain which is thought to be cytoplasmic. If the v-erb-B sequence was acquired from the gene encoding the EGF receptor then the v-erb-B protein represents a truncated receptor which lacks the EGF binding domain. It is particularly interesting that studies of EGF receptor biosynthesis in A431 cells have suggested that a polypeptide equivalent to the external domain of the receptor (of molecular weight 115,000) is synthesised (50) in addition to the normal receptor. Further studies are necessary to understand the origin of this truncated receptor but the results show that defective receptors may be synthesised by this human tumour cell line.

GROWTH FACTORS AND TRANSFORMATION

Recently it has been shown that the transforming protein of simian sarcoma virus has a close structural and functional relationship to the growth factor PDGF (7-10) supporting the hypothesis that autocrine growth factor production may be involved in abnormal growth control and neoplasia. These observations together with those presented here illustrate two distinct but related mechanisms for subversion of normal growth regulation. In the case of SSV the oncogene encodes a growth factor which can act as a mitogen for target cells having PDGF receptors (10). AEV on the other hand appears to have employed a different mechanism where a part of a growth factor receptor which is thought to be involved in transducing the EGF signal may be expressed in transformed cells. The absence of the EGF binding domain might remove the control generated by ligand binding and the result could be the continuous generation of a signal equivalent to that produced by EGF, causing cells to proliferate rapidly. How this could result in the block in differentiation observed in AEV infected haemopoietic cells (61) is unclear. However EGF has been shown to promote proliferation while inhibiting terminal differentiation of human keratinocytes (31).

The ES4 strain of AEV has two oncogenes v-erb-A and v-erb-B, which are thought to encode proteins of MWs 75,000 and 65,000 respectively (for a recent review see 62). Cells transformed by AEV in vitro and in vivo have the properties of erythroblasts which are late erythroid progenitors, although the target cells themselves may be earlier erythroid precursor cells. AEV can also transform fibroblasts and induce sarcomas. Evidence from deletion mutants (63) and from an isolate (AEV-H (30)) which lacks the v-erb-A gene suggests that the v-erb-B gene alone can induce transformation. This is supported by studies which show that RAV-1, a leucosis virus which has no oncogene, can activate the c-erb-B gene by a promoter insertion mechanism (64) perhaps similar to that presently being unravelled for c-myc activation (65-67). It is possible that RAV-1 could induce expression of a normal receptor or a truncated receptor. EGF receptors have not generally been detected on haemopoietic cells by EGF binding studies but since these studies are limited in scope and sensitivity a more rigorous survey is needed before conclusions about normal receptor expression in different haemopoietic cell types can be made. Although many normal cells express 10–100,000 EGF receptors (31) only very low levels of c-erb-B transcripts have been found in normal chicken fibroblasts (51), however a recent study of normal and neoplastic human lymphocytes suggests that both types of cells contain c-erb-B related transcripts.

Previous reports have shown that the predicted amino acid sequences of the putative viral transforming proteins encoded by the oncogenes erb-B, src, yes, fes, fps, mos and abl show regions of homology (29,30,69). In the case of src, yes, fes, fps and abl the putative transforming proteins have been shown to have tyrosine kinase activity (reviewed in 29) but as yet those encoded by erb-B (30) and mos have not. Since the receptors for EGF and αTFG, PDGF, insulin and IGF-I also have associated tyrosine kinases, the structural relationship between the v-erb-B transforming protein and the EGF receptor observed here, we believe that other oncogenes from this subset of retroviruses are derived in part from sequences encoding these or other growth factor receptors.

The diagnostic methods used in assaying the EGF receptor, its truncations and antibodies thereto are conventional. These include the competitive, sandwich and steric inhibition techniques. The first two methods employ a phase separation step as an integral part of the method while steric inhibition assays are conducted in a single reaction mixture. The methodology for assay of the EGF receptor or its truncations on the one hand and for substances that bind the receptor or its truncations on the other are essentially the same, although certain methods will be favoured depending upon the size of the substance being assayed. Therefore the substance to be tested is referred to herein as an analyte, irrespective of its status otherwise as an antigen or antibody, and proteins which bind to the analyte are denominated binding partners, whether they be antibodies, receptors or antigens.

Analytical methods used herein all employ one or more of the following reagents: labelled analyte analogue, immobilised analyte analogue, labelled binding partner, immobilised binding partner and steric conjugates. The labelled reagents also are known as "tracers".

The label used is any detectable functionality which does not interfere with the binding of analyte and its binding partner. Numerous labels are known for use in specific binding assays, examples including enzymes such as horseradish peroxidase, radioisotopes such as $^{14}C$ and $^{131}I$, fluorophores such as rare earth chelates or fluorescein, spin labels and the like. Conventional methods are available to covalently bind these labels to proteins or polypeptides. Such bonding methods are suitable for use with EGF receptors, their truncations and antibodies thereto, all of which are proteinaceous.

Immobilisation of reagents is required for certain assay methods. Immobilisation entails separating the binding partner from any analyte which remains free in solution. This conventionally is accomplished by either insolubilising the binding partner or analyte analogue before the assay procedure, as by adsorption to a water insoluble matrix or surface (Bennich et al., U.S. 3,720,760) or by covalent coupling (for example using glutaraldehyde cross-linking), or by insolubilising the partner or analogue afterward, e.g., by immunoprecipitation.

Steric conjugates are used in the steric hinderance method for homogeneous assay. These conjugates are synthesised by covalently linking a low molecular weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate resulting in a change in the character of the conjugate hapten, e.g., a change in fluorescence when the hapten is a fluorophore.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner generally is insolubilised before or after the competition and then the tracer and analyte bound to the binding partner are separated from the unbound tracer and analyte. This separation is accomplished by decanting (where the binding partner was preinsolubilised) by centrifuging (where the binding partner was precipitated after the competitive reaction). The amount of test sample analyte is inversely proportional to the amount of bound tracer as measured by the amount of marker substance. Doseresponse curves with known amounts of analyte are prepared and compared with the test results in order to quantitatively determine the amount of analyte present in the test sample. These heterologous assays are called ELISA systems when enzymes are used as the detectable markers.

Another species of competitive assay, homogeneous assay, does not require a phase separation. Here, a conjugate of an enzyme with the analyte is prepared so that when anti-analyte binds to the analyte the presence of the anti-analyte modifies the enzyme activity. In this case, the receptor or its immunologically active fragments are conjugated with a bifunctional organic bridge to an enzyme such as peroxidase. Conjugates are selected for use with anti-receptor so that binding of the anti-receptor inhibits or potentiates enzyme activity. This method per se is widely practiced under the name EMIT.

Sandwich assays particularly are useful for the determination of the analytes hereof. In sequential sandwich assays an immobilised binding partner is used to adsorb test sample analyte, the test sample is removed as by washing, the bound analyte is used to adsorb labelled binding partner and bound material then separated from residual tracer. The amount of bound tracer is directly proportional to test sample analyte. In "simultaneous" sandwich assays test sample is not separated before adding the labelled binding partner.

The foregoing are merely exemplary assays for the analytes herein. Other methods now or hereafter developed for the determination of these analytes are included within the scope hereof.

FIGURE LEGENDS to FIGS. 1–5

FIG. 1. Immunopurification of EGF receptor from A431 cells and human placenta.

Approximately $2 \times 10^9$ A431 cells were washed in calcium and magnesium free phosphate buffered saline (PBS) and solubilised in 400 ml lysis buffer (50 mM Tris HCl pH 7.4, 0.15M NaCl, 5 mM EGTA, 0.1% bovine serum albumin, 1% NP40, 25 mM benzamidine, 0.2 mM PMSF, 10 μg/ml leupeptin). After filtration through muslin the lysate was adjusted to pH 8.5 and centrifuged at 100,000 $g_{max}$ for 30 minutes. The supernatant was incubated for 2 hours at 4° C. with immunoaffinity matrix, which consisted of 15 mg of monoclonal antibody R1 (34) coupled to 15 ml of Affi-Gel 10 (BioRad). Unbound lysate was removed by suction through a 0.4 micron filter. The matrix was then washed by gentle agitation and filtration with 500 ml PBS, containing 0.65M NaCl and 0.1% NP40, followed by 500 ml PBS, containing 0.1% NP40. The EGF receptor was eluted by gentle agitation and filtration of the matrix with 2×10 ml aliquots of 50 mM sodium citrate pH 3, containing 0.05% NP40 for 10 minutes each. Eluates were adjusted to pH 7. The yield of receptor was approximately 250 μg (measured by Bradford technique (70) or by amino acid analysis after gel permeation HPLC (vide infra)). Alternatively EGF receptor was purified from A431 cells using monoclonal antibody 29-1 (38) coupled to CNBr-activated Sepharose (Pharmacia) at 5–10 mg/ml. The purification procedure used was similar to that described for the R1 immunoaffinity matrix except that the EGF receptor was phosphorylated whilst bound to the matrix with 50 μCi($\gamma$-$^{32}$P)-ATP (3,000 Ci/mmol, Amersham International) in the presence of 3 mM MnCl$_2$. Eluted receptor was further purified by preparative SDS gel electrophoresis, followed by dialysis against 10% methanol at 4° C. For purification of placental EGF receptor, vesicles were made from syncytiotrophoblastic microvilli by a modification of the method of Smith et al. (71), using 2 mM EGTA in all buffers. Vesicles were solubilized by addition of an equal volume of 100 mM Hepes pH 7.4, 0.15M NaCl and 5% Triton X-100. After centrifuging at 100,000 $g_{max}$ for 30 minutes the supernatant was incubated for 1 hour at room temperature with 200 mg wheat germ agglutinin coupled to 10 g of Affi-Gel (Bio/Rad). The lectin matrix was washed by filtration through a 0.4 micron filter with 100 ml of PBS, containing 0.1% Triton X-100. Bound protein was eluted by agitation and filtration with 2×15 ml aliquots of 0.25M N-acetylglucosamine in 10 mM Hepes pH 7.4, 0.1% Triton X-100 for 15 minutes each. The eluate was incubated with R1 immuno-affinity matrix (15 mg antibody per placenta) for 2 hours at 20° C., followed by extensive washing and elution as described above for receptor purification from A431 cells. The yield of EGF receptor per placenta was 25 μg (measured by Bradford technique (70) and amino acid analysis after gel permeation HPLC (vide infra)).

Solutions containing EGF receptor were lyophilized and resuspended in 0.5M Tris HCl pH 8.5, 6M guanidine hydrochloride (Schwarz-Mann) at 0.5–1 mg/ml. After incubation at 37° C. for 16 hours with 10 mM dithiothreitol, cysteine residues were alkylated with [$^{14}$C]-iodoacetamide (40–60 mCi/mmol, Amersham International) as described previously (44).

(A) Purification by gel permeation: Reduced and alkylated receptor was purified on a TSK4000 column (0.7×60 cm, LKB) using 0.1M potassium dihydrogen phosphate buffer pH 4.5 containing 6M guanidine HCL at a flow rate of 0.5 ml/min (43). The absorbance of the eluate was monitored at 280 nm (molecular weights of protein standard are indicated) and 0.25 ml fractions were collected. Fractions containing EGF receptor were dialyzed against 10 mM ammonium bicarbonate. Panels B-D show 7% polyacrylamide SDS gels (72) used to monitor purification (molecular weight ($\times 10^{-3}$) of protein standards are indicated).

(B) R1 purified A431 EGF receptor: track 1, pH 3 eluate from R1 immunoaffinity matrix; track 2, eluate from the TSK4000 column (C) 29-1 purified A431 EGF receptor: track 1, pH 3 eluate from 29-1 immunoaffinity matrix: track 2, eluate from SDS preparative gel electrophoresis.

Figure 2:
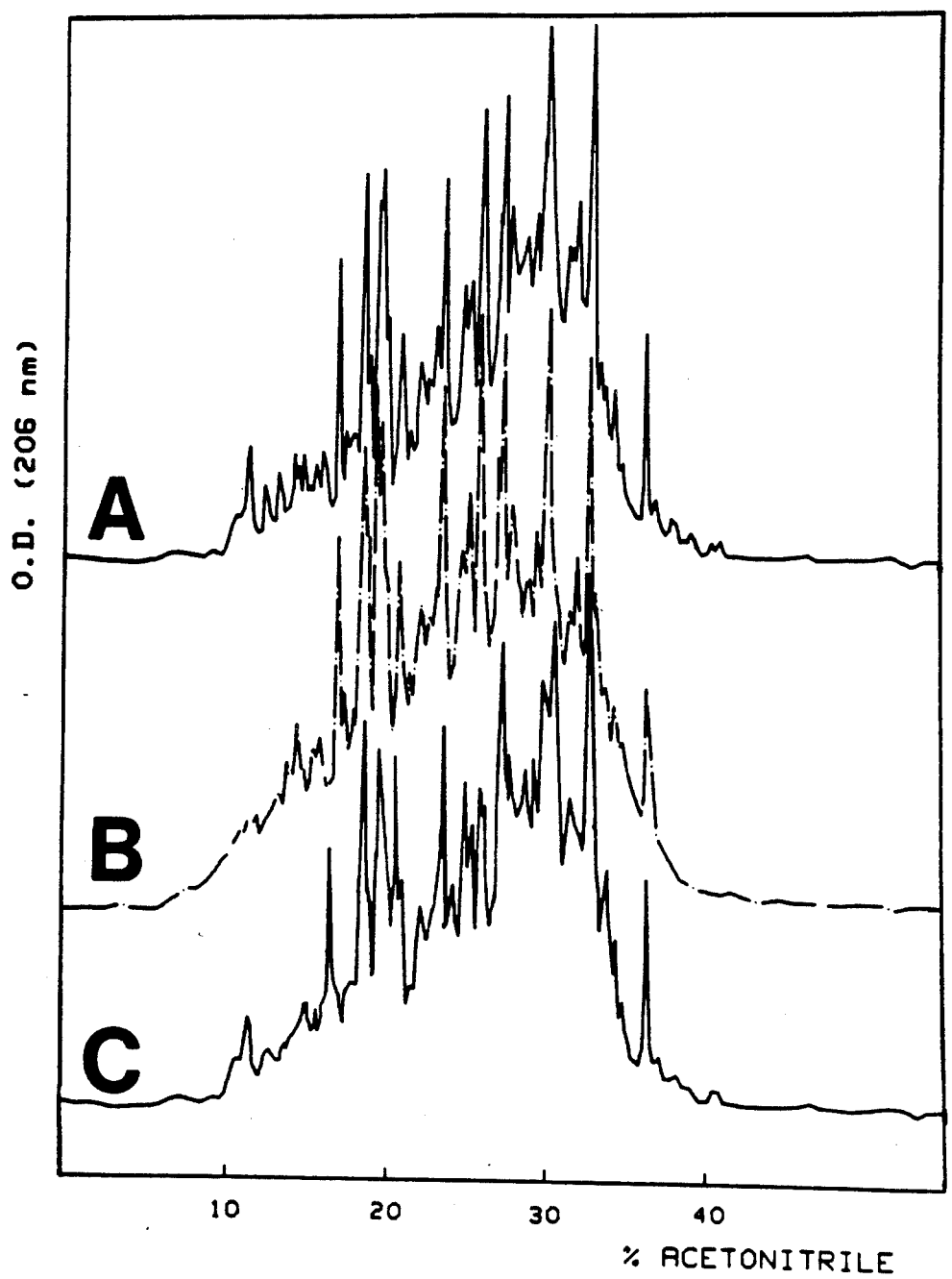
FIG. 2 shows the optical density of an eluate at 206 nm plotted against acetonitrile concentration in reverse phase HPLC analysis of tryptic peptides from EGF receptor.
Figure 3B:
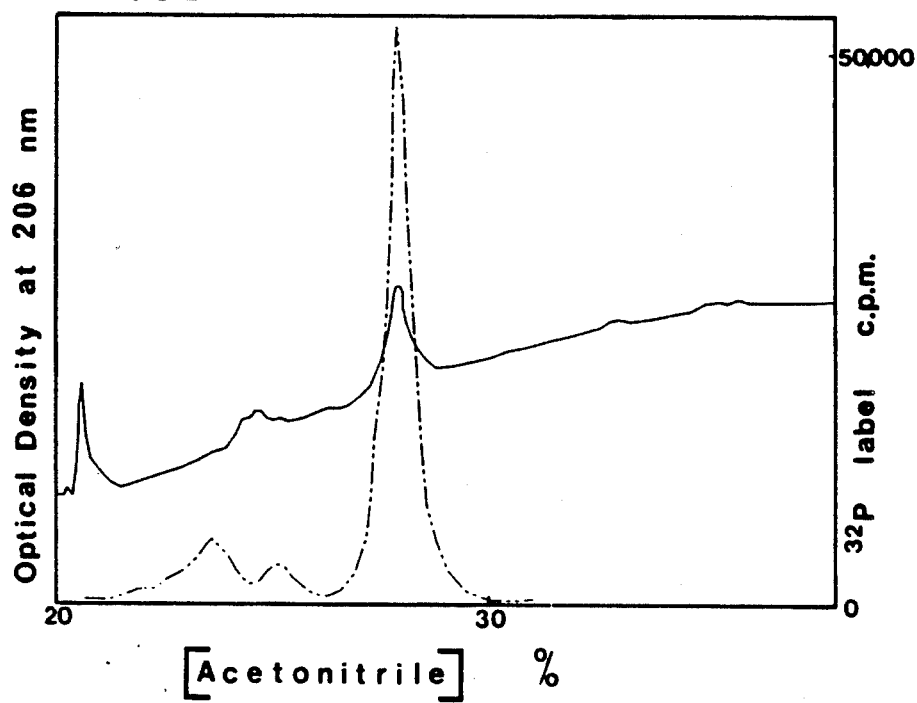

(D) Lectin and R1 purified placental EGF receptor: track 1, placental vesicles; track 2, eluate from lectin affinity matrix; track 3, eluate from R1 immunoaffinity matrix; track 4, eluate from the TSK4000 column FIG. 2. Reverse phase HPLC analysis of tryptic peptides from EGF receptor purified by three different affinity methods.

A. Immunoaffinity purified A431 receptor, EGF receptor was purified from A431 cells using the monoclonal antibody R1 and then gel permeation chromatography in guanidine solutions as described in FIG. 1. Pooled fractions containing the 175,000 MW EGF receptor were dialyzed against 10 mM ammonium bicarbonate, lyophilized and resuspended in 500 μl of 100 mM ammonium bicarbonate, 10 mM CaCl$_2$. TPCK treated trypsin (Sigma) was then added (100:1, receptor:trypsin, w/w). This mixture was incubated at 37° C. for 12 hours, a further identical aliquot of trypsin added and the incubation continued for another 12 hours. Peptides were then loaded directly onto a Synchropak RPP C18 reverse phase HPLC column (Synchrom, Linden, Ind., 4.6×75 mm) equilibrated in 0.1% trifluoroacetic acid (TFA, Rathburn, Scotland) over 45 minutes at 1 ml/min and 1 ml fractions collected (46). A Waters HPLC system including two M6000 A pumps, a U6K manual injector, a 660 solvent programmer with 2 LKB 2138 Uvicord S absorbance detectors with filters at 206 nm and 280 nm was used (45). The figure shows the optical density of the eluate at 206 nm plotted against acetonitrile concentration.

B. EGF affinity purified receptor, EGF receptor was purified from A431 cells using wheat germ agglutinin affinity chromatography followed by EGF affinity chromatography (26). A431 cells were lysed as described in the legend to FIG. 1. Purification of this lysate on the WGA affinity column was identical to that described for the placental preparation (FIG. 1). The eluate from the WGA affinity column was mixed with 5 ml of Affi-Gel 10 (BioRad) having 1 mg of bound EGF. The mixture was tumbled for four hours at room temperature prior to washing the immobilized EGF receptor with 100 ml of PBS, 0.1% Triton X-100. Receptor was then eluted with 10 mM ethanolamine, pH 9.7, 0.1% Triton X-100. This eluate was further purified on a TSK4000 gel permeation column as described in FIG. 1. Fractions containing EGF receptor were pooled, dialyzed, lyophilized and trypsinized as described for A above. The resulting tryptic peptides were separated by reverse phase HPLC under identical conditions to those described above.

C. Immunoaffinity purified placental receptor, EGF receptor was purified from fresh term human placenta as described in the legend to FIG. 1. The receptor was digested with trypsin and peptides separated by reverse phase HPLC as described above.

FIG. 3. Purification of peptides from EGF receptor for sequence analysis.

A. Cyanogen Bromide cleavage and fractionation of peptides by size $^{32}$P-labelled EGF receptor in ammonium bicarbonate solution was lyophilized and resuspended in 70% formic acid. Cyanogen bromide was added under nitrogen, the tube sealed and incubated in the dark at room temperature for 24 hours. Formic acid and excess cyanogen bromide were removed by repeated cycles of drying and resuspension in water using a Speed-vac concentrator (Savant). The dry sample was resuspended in 0.1M KH$_2$PO$_4$ buffer, pH 4 containing 6M guanidine HCl and the peptides separated by gel permeation HPLC on a TSK3000 column (0.7×60 cm, LKB) equilibrated in the same buffer at a flow rate of 0.3 ml/min (43). The absorbance of the eluate was monitored at 280 nm (— —) and 0.3 ml fractions collected and counted for $^{32}$P (—..—). Molecular weights (×10$^{-3}$) of protein standards are indicated.

B. Subfractionation of cyanogen bromide fragments

The peak from the TSK3000 column containing most of the $^{32}$P-label was pooled and dialyzed against 10 mM NH$_4$HCO$_3$. After lyophilization, the sample was redissolved in 0.1% TFA and peptides separated by reverse phase HPLC on a Synchropak RPP C18 (see FIG. 2) column equilibrated in 0.1% TFA, 10% acetonitrile (45,46). A gradient of 10–40% acetonitrile run over 60 minutes was used to elute peptides, at a flow rate of 1 ml/min. The absorbance of the eluate was monitored at 206 nm (— —) and 1 ml fractions were collected and counted for $^{32}$P-label (—..—).

C-F. Separation of tryptic peptides.

C. The fractions corresponding to 23–24% acetonitrile from the HPLC analysis of A431 EGF receptor tryptic peptides were pooled. Peptides were further purified by reverse-phase HPLC on a Synchropak RPP C18 column equilibrated in 10 mM ammonium acetate buffer pH 6.5. A linear gradient of 0–45% acetonitrile was run over 45 minutes at a flow rate of 1 ml/min. The absorbance of the eluate was monitored at 206 nm and 0.5 ml fractions collected.

D. The fractions corresponding to 19–20% acetonitrile from the reverse-phase HPLC purification of A431 EGF receptor tryptic peptides of (FIG. 2A) were pooled. Peptides were separated as described in C.

E. The peak fractions arrowed in D were pooled and peptides subfractionated by reverse-phase HPLC on a μ Bondapak phenyl column (4.6×25 cm, Waters Assoc.) equilibrated in 0.1% TFA. A linear gradient of 0–45% acetonitrile over 45 minutes was used to elute peptides, at a flow rate of 1 ml/min. The absorbance of the eluate was monitored at 206 nm and 0.2 ml fractions collected.

F. The fractions corresponding to 27–28% acetonitrile concentration from the reverse-phase HPLC analysis of placental EGF receptor tryptic peptides (FIG. 2C) were pooled. Peptides were subfractionated as described in C.

G. The fractions corresponding to 25–26% acetonitrile from the reverse-phase HPLC purification of A431 EGF receptor tryptic peptides (FIG. 2A) were pooled. Peptides were subfractionated as described in C.

H. The fractions corresponding to 21–22% acetonitrile from the reverse-phase HPLC analysis of A431 EGF receptor tryptic peptides (FIG. 2A) were pooled. Peptides were subfractionated as described in C.

FIG. 4. Sequence analysis of peptides from the EGF receptor

Peptides were purified as described in FIG. 3. Sequence determination of each peptide was carried out using a gas phase sequencer assembled and operated as described by Hewick et al., (47). PTH amino acids were analyzed by HPLC using a Zorbax C8 column (4.6×150 mm, Dupont) at 43° C. with a linear gradient over 8 mins of acetonitrile from 24% to 38% at a flow rate of 1 ml/min using 9 mM sodium acetate buffer pH 4.1 (48). A Waters HPLC system including two M6000 A pumps, a WISP autoinjector and system controller with a Beckman Model 160 detector was used. The recovery of PTH amino acids at each degradative cycle was measured using an integrative recorder (Waters Data module). The amounts of each peptide analysed were measured by the recovery at step 1 during amino acid sequencing. The analysis for serine and threonine could not be accurately measured due to the presence of multiple peaks obtained during analysis of the PTH amino acids. The presence of these amino acids is thus indicated without quantitative data; these residues are assigned to the sequence using semi-quantitative recovery data based on peak heights rather than areas. Prior to loading peptides, fibre glass disks were treated with polybrene and glycylglycine and precycled for ten cycles. Each peptide was sequenced twice; on the second run of peptide EGRC.1 filters were treated with polybrene and cysteic acid and precycled ten times to clarify the assignment of an amino terminal glycine residue, however the background glycine at step 1 is still significant and this residue may be incorrect.

FIG. 5. The relationship between the amino acid sequences of the EGF receptor peptides and the predicted amino acid sequences of the putative transforming proteins of v-src and v-erb-B.

The predicted amino acid sequence of the v-src gene product (pp60$^{v-src}$) is translated from the presumptive initiation codon at nucleotide 7,129 of the Prague C strain of Rous sarcoma virus (73). The predicted amino acid sequence of the v-erb-B gene product is translated from the presumptive initiation codon at nucleotide 155 of the v-erb-B gene in AEV-H (30). The partial amino acid sequences of the six peptides purified from the EGF receptor are shown (underlined): 1, EGRT.1; 2, PTER.1; 3, EGRT.10; 4, EGRT.2; 5, EGRC.1; 6, EGRT.9. Letters in bold type represent homologous residues between pp60$^{v-src}$ and the v-erb-B protein. Residues homologous between the EGF receptor peptides and v-erb-B protein or pp60$^{v-src}$ are in bold type. indicates amino acid residues which are common to the putative transforming proteins of v-erb-B, v-src, v-fes, v-fps, v-yes and v-abl. indicates the phosphoacceptor tyrosine of pp60$^{v-src}$ (74). An arrowhead indicates possible N-linked glycosylation sites at the amino terminus of the v-erb-B protein. indicates the putative transmembrane sequence in the v-erb-B protein. indicates amino acid residues which would be expected to produce enzymatic or cyanogen bromide cleavages to generate the observed peptides. Numbers to the left of the sequences are residue numbers taking the presumptive initiation methionine as 1 in both cases. Sequences were aligned using a computer programme (75) to optimise homology.

The invention should not be construed as limited to the scope of the following Examples, but rather is defined by the claims.

EXAMPLE 1

Generation of Antisera Against a Predetermined EGF Receptor Amino Acid Sequence

A polypeptide corresponding to amino acid residues 984–996 of the EGF receptor (DDVVDADEYLIPQ)

was synthesized according to the Merrifield solid phase synthesis technique (R. Merrifield 1963, "J. Am. Chem. Soc." 85, 2149-2154) with some modifications (R. Buchta, 1982, Chemical Studies on proposed calcium binding sites of polypeptides, M. Sc. Thesis, Fineberg Graduate School, Weizmann Institute of Science, Rehovot, Israel). These residues represent a polypeptide sequence located just C-terminal to the region of EGF receptor homology shared by the putative kinase domain of the SVC gene family. Following separation of the completed peptide from the resin by cleavage with HF, the peptide was partially purified by gel filtration with G-15 (Sephadex). The sequence was confirmed by gas phase sequencing.

Immunization

The peptide was conjugated to KLH (Keyhole limpet hemocyanin, Calbiochem) by using 1-ethyl-3-(3'-dimethylaminopropyl)carbodiimide:HCl (EDCI). KLH dialysed against PBS, pH 7.2, was mixed with 40 times molar excess of the peptide dissolved in PBS. After mixing at room temperature for five minutes, EDCI (10×molar excess over the peptide) in $H_2O$ was added to start the reaction which was mixed overnight at room temperature. The resulting complex was dialysed against PBS. One mg of this conjugate was emulsified with complete Freund's adjuvant and injected subcutaneously into multiple sites of two rabbits. Two boosts in incomplete Freund's adjuvant two weeks apart were also injected subcutaneously. Two weeks following the last injection the rabbits were bled and RK-2 antiserum recovered.

This antiserum was found to not interfere with the kinase activity of the receptor.

Other antisera having differing specificities are obtained by conjugating EGF receptor polypeptides, generally about from 5 to 20 residues in length, to KLH or other suitable immunogenic proteins such as bovine serum albumin and immunising rabbits, mice or other animals. The conjugation generally will be effected through amino, hydroxyphenyl, carboxyl or sulfhydryl groups found on the polypeptide and the protein using well-known bifunctional crosslinking agents such as those described in the Table below.

TABLE

| Peptidyl or Protein Reactive Group(s) | Coupling Agent | Peptidyl or Protein Reactive Group(s) |
|---|---|---|
| $-NH_2$ | glutaraldehyde | $-NH_2$; $-OH$ |
| $-NH_2$ | succinic anhydride | $-NH_2$ |
| $\overset{O}{\underset{\|}{-C-NH_2}}$ | $H_2N-NH_2$, $HNO_2$ | $-NH_2$; $-SH$; $-OH$ |
| $-NH_2$; SH | $R'N=C=NR$ | $-COOH$ |
| $-COOH$ | $SOCl_2$ | $-COOH$ |
| $-COOH$ | N-hydroxysuccinimide | $-NH_2$ |

The antisera raised upon immunisation are then screened for their ability to cross-react with native EGF receptor. Spleen cells from immunised mice are harvested, fused with tumour cells and cultured in conventional fashion in order to produce monoclonal antibodies.

EXAMPLE 2

Immunoassay For Truncated EGF Receptor in Human Test Samples

Tumour cells were washed twice with PBS (phosphate buffered saline) and solubilised in 1 ml of solubilisation buffer containing: 20 mM $MgCl_2$, 1.0 mM EDTA, 1 percent aprotinin. The solubilised cells were centrifuged in an eppendorf centrifuge for 10 minutes at 4° C. The supernatant was diluted to a final concentration of 0.1 percent Triton X-100 and 300 ul of this solubilised cell preparation was incubated overnight at 4° C. with an excess of an immune complex made by adsorbing human EGF to a polyclonal rabbit anti-human EGF antisera adsorbed on Sepharose-protein A. Parenthetically, it is preferable in place of immobilised EGF to use an antibody raised against a sequence within (or all of) the first about 500 residues of the EGF receptor principally because some of the receptors in biological samples can be expected to already be bound to EGF and therefore not have an available EGF binding site. Any excess anti-human EGF antiserum over EGF will have the capability to bind receptor-bound EGF, but the kinetics of this reaction may be undesirable. Suitable antibody will be identified readily by its resistance to competition by EGF for receptor binding. Use of this antibody will result in a more sensitive assay.

The supernatant cell preparation was recovered by centrifugation and then incubated at 4° C. for 30 minutes with Sepharose-Protein A adsorbed RK-2 antisera in order to bind truncated EGF receptor. The Sepharose immunoadsorbent then was incubated with radioiodinated Fab fragments of RK-2 antisera prepared in conventional fashion by purifying the enzyme digested antisera and iodinating the fragments with $125^I$ using the chloramine T procedure. The unadsorbed tracer Fab fragments were washed from the Sepharose and the remaining radioactivity determined in a commercial gamma counter as a measure of the truncated receptors present, if any. Placental cells were used as contols.

This Example was repeated with modifications for the determination of truncated EGF receptor in blood serum from patients suspected of harbouring cancer. Patient serum was passed through a column packed with a Sephadex-adsorbed immune complex of polyclonal rabbit anti-human EGF anti-serum and human EGF. Alternatively usable and preferred are antisera raised against a polypeptide from within, or against all of the first about 500 residues of the mature EGF receptor as is further described above. The eluted serum then is assayed in a competitive immunoassay in which radioiodinated EGF receptor is allowed to compete with any truncated EGF receptor in the test sample for Sepharose-Protein A adsorbed RK-2 antisera, the Sepharose washed and the radioactivity in the eluate or Sepharose then determined. The v-erbB protein of AEV-H, $p67^{erbB}$ (T. Yamamoto et al, 1983 "Cell" 35: 71-78), is a suitable positive control because RK-2 cross-reacts with v-erbB.

EXAMPLE 3

Determination of EGF Receptor Population in Human Test Samples

Buffered dilutions of human serum from patients suspected of harbouring cancer were prepared. RK-2 adsorbed, pooled normal serum and solubilised A431 EGF receptors served as negative and positive controls, respectively. EGF receptors shed into the serum by tumour cells were detected by incubating the serum dilutions in polystyrene test tubes or microtiter wells which had been coated sequentially in conventional fashion with goat anti-rabbit IgG and then RK-2 antiserum. Alternatively, an immune precipitate of these antibodies may be employed in place of immobilisation onto polystyrene test tubes. After an overnight incubation the tubes were washed to remove unadsorbed sample and then a buffered solution of an excess of radioiodinated $R_1$ monoclonal antibody is added to the test tube. $R_1$ is an antibody that recognises the outer glycosylated portion of the EGF receptor as described in M. Waterfield et al., "J. Cell. Biochem." 30: 753-757 (1982). An antiserum or antibody having the characteristics of $R_1$ is preferred as it binds to an EGF receptor site that is spatially separated from the cytoplasmic domain to which RK-2 is directed and it is not believed to be competitively inhibited by EGF in binding to the receptor. Such antiserum is prepared in accordance with known procedures as noted above.

Unbound tracer is removed from the test tube by decanting and washing. The radioactivity in the decanted solution or that which remains bound to the test tube is compared against the results of a plot of known solubilised EGF receptor concentrations and the serum concentration then calculated. Consistently elevated concentrations of receptor, compared to controls, are an incidia of potential unknown neoplasm, or further growth or metastasis of a known neoplasm.

EXAMPLE 4

Antibody-Toxin Conjugate

Anti-receptor IgG raised in rabbits by immunisation with a KHL conjugate to the polypeptide AHYINDGPHCVKTCPAGVMGENNTLV-WKYADAGHVCHLCHPACTYGCTGPGLE GCPTNGPKIPS (RK-3), was purified by fractional ammonium sulphate precipitation, resolubilisation in PBS at pH 7, adsorption onto solubilised EGF receptor from A431 cells which had been immobilised on cyanogen bromide-activated Sepharose and elution at pH 4.8. Purified antiserum or $R_1$ monoclonal antibody (see above) were linked to Vindesine following the procedure of EP 56322A. Alternatively the antibodies were conjugated to ricin subunit A (EP 63988A or EP 23401A), diptheria toxin (WO 8304026A) or a toxic enzyme (EP 89880A). See also EP 44167A, EP 55115A, U.S. Pat. No. 4,379,145, EP 74279A or EP 94815A. Similar techniques were employed to conjugate radio-opaque dyes to the antibodies. A panel of human tumour established cell lines shown by cytoimmunofluorescence with fluorescein labelled $R_1$ antibody to contain a large number of cell surface EGF receptors was selected, along with A431 carcinoma cells. The tumour cells were established in nude mice and varying concentrations of toxin or radio-opaque conjugates infused into a tail vein in sterile physiological saline or other pharmaceutical carrier.

The presence of high numbers of receptors in candidate cells was determined as follows. Equal amounts (25 mg) of tissue from candidate cells or tissues were solubilised as described by Libermann et al., "Cancer Res." 44: 753-760 (1984). Equal amounts of protein as determined by the method of Bradford ("Anal. Biochem." 72: 248-254) were used for immunoprecipitations with either polyclonal rabbit antibodies generated against membranes enriched with EGF receptor from the A431 cell line (Libermann et al., op. cit), or the polyclonal rabbit antibodies RK-2 described above. Functional EGF receptor kinase was immunoprecipitated and detected by phosphorylation of the immunoprecipitate using (gamma-$^{32}$P)ATP according to Libermann et al., op cit. The immunoprecipitates were dissolved in electrophoresis sample buffer and electrophoresed in a 5-15% SDS-polyacrylamide gel. The gel was dried and autoradiographed for 12 hours at room temperature. A431 cells were used as a standard source for the EGF receptor. The arrowhead indicates the position of the EGF receptor. High molecular weight markers used were: light chain of IgG (25kd), heavy chain of IgG (50kd), bovine serum albumin (66.2kd), phosphorylase B (94kd), -galactosidase (116kd) and myosin heavy chain (200kd)(Biorad). High levels of EGF receptor expression was indicated by $\geq$20,000 cpm.

EXAMPLE 5

Administration of Receptor Fragments to Carcinoma Cells

The EGF receptor polypeptide fragments ELVEPLTPSGEAPNQALLR; VLGSGAFGTVYK; GLWIPEGEK; VLVIQGDER; DVVDADEYLIPQ; DVVDADEYLIPQQGFF; AEEKEYHAEG; (EAY)n where n>1; or GSHQISLDNPDYQQDFF were synthesised by the method described in Example 1. The fragments were dissolved in a conventional carrier at varying dilutions, sterile filtered, injected into A431 cells by standard micro-injection techniques and the effect on cell growth and morphology was observed.

EXAMPLE 6

Detection of mRNA and Amplified DNA in Cells

The DNA sequence encoding the EGF receptor was described in A. Ullrich et al., "Nature" 309: 418-425 (1984). Amplification of the EGF receptor gene in human glioblastoma and A431 DNA was detected by Southern blot analysis of DNA from primary human brain tumours, A431 epidermoid carcinoma cells and human placenta. The DNA from these tumours was digested with EcoRI and probed with $^{32}$P-labelled p8.4 DNA. Referring to FIG. 6, GM1 and GM2 are different primary human glioblastomas, MEN1 is a meningioma, A431 is a human epidermoid carcinoma cell line and HPL is human placenta which served as a control tissue.

METHODS:

a. EGF receptor cDNA clone p8 was obtained as follows: mRNA from A431 cells was isolated with the guanidine thiocyanate/cesium chloride method (*T. Maniatis, Molecular Cloning*, 1982). cDNA synthesis, cloning into pUC9, and colony screening were carried out according to published protocols (D. Helfman, 1983, "Proc. Nat. Acad. Sci. USA" 80: 31-35). Briefly, a 17mer probe, as a mixture of 256 oligonucleotides (3'ATA/G TTA/G GGX TGX TGX AT5') based on the amino acid sequence of a tryptic peptide of A431 EGF receptor, was end-labelled with T4 polynucleotide kinase (New England Biolabs) and (gamma-$^{32}$P)ATP (Amersham, 3000 Ci/mmol). Colony screening hybridisation was carried out in 6xSSC, 5xDenhardt, 0.1% SDS, 100 µg/ml salmon sperm DNA at room temperature for 36 hours. Filters were washed at 45° C. with 3xSSC, 0.1% SDS. Nucleotide sequence analysis was carried out according to Maxam and Gilbert, *Methods Enzymol.* 65: 499-550 (1980). p8 is a 2.5kb cDNA clone derived from the 2.8kb variant mRNA from A431 cells described by Ullrich et al., op. cit. p8.4 is a Pst fragment (399bp) derived from clone p8. Other DNA fragments of the EGF receptor gene also are suitable as probes.

B. High molecular weight chromosomal DNA from test cells was isolated as described (Maniatis, op. cit). DNA (15 microgram) was digested to completion with excess of either EcoRI or HindIII (New England Biolabs), fractionated by electrophoresis through a 0.7% agarose gel and transferred to nitrocellulose paper. The Pst insert of p8.4 (p8) was radiolabelled with (gamma-$^{32}$P)dATP and (gamma-$^{32}$P)aCTP (Amersham) by the procedure of Taylor et al., "Biochem. Biophys. Acta" 4: 324–330 (1976). Hybridisation with $10^7$ c.p.m. of $^{32}$P-labelled probe was performed in 6×SSC, 5×Denhardt, 10% dextran sulphate, 50 mM sodium phosphate pH 6.5 and 100 μg/ml salmon sperm DNA at 65° C. for 16 hours. Filters were washed in 0.2×SSC, 0.1% SDS at 65° C. and autoradiographed for one day at −70° C. using intensifier screens. Sizes were calculated using α phage DNA cleaved with restriction endonuclease HindIII as standards.

Figure 6A:
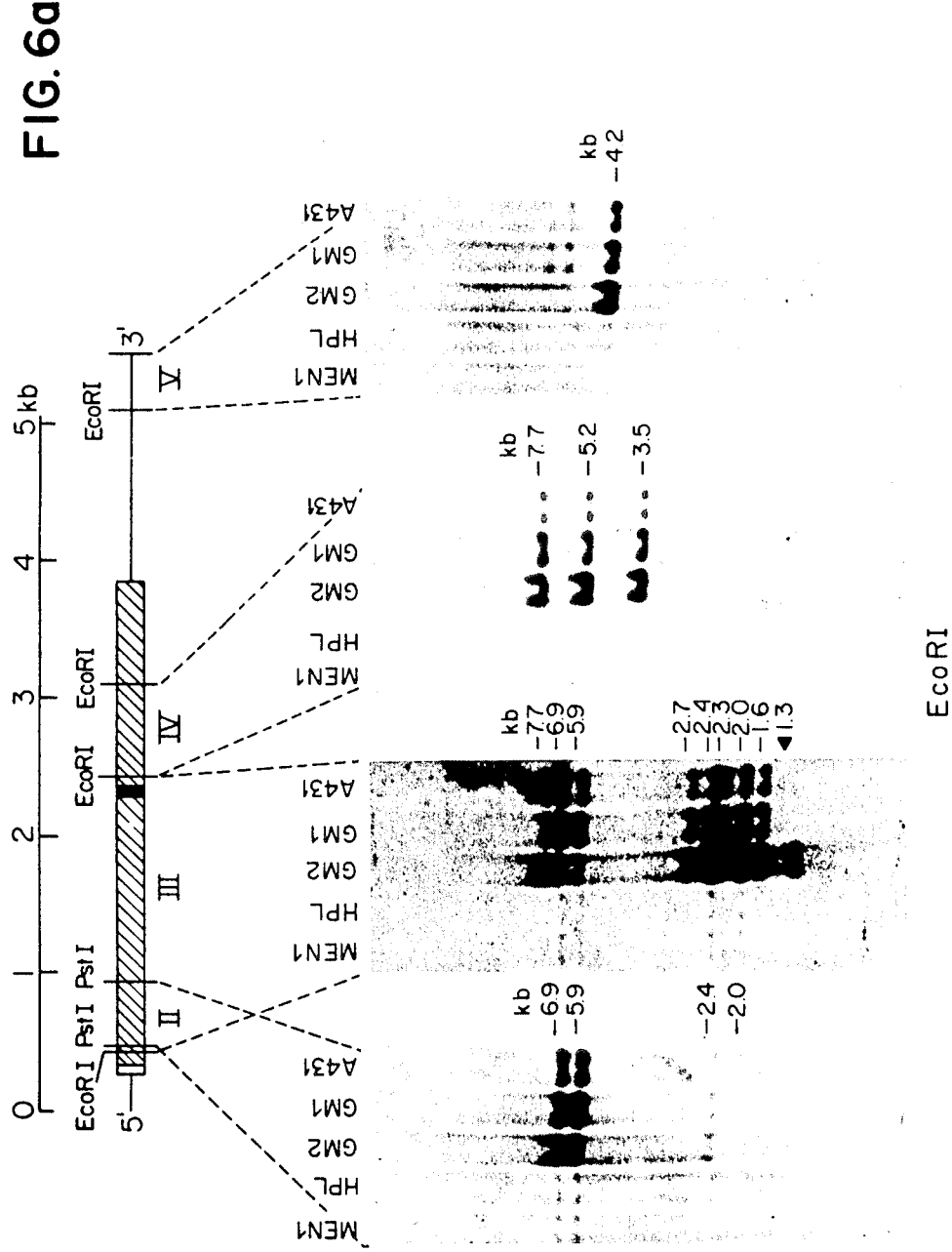
FIG. 6 shows Southern blot hybridisation analysis of DNA from various normal and tumour tissues.
Figure 6B:
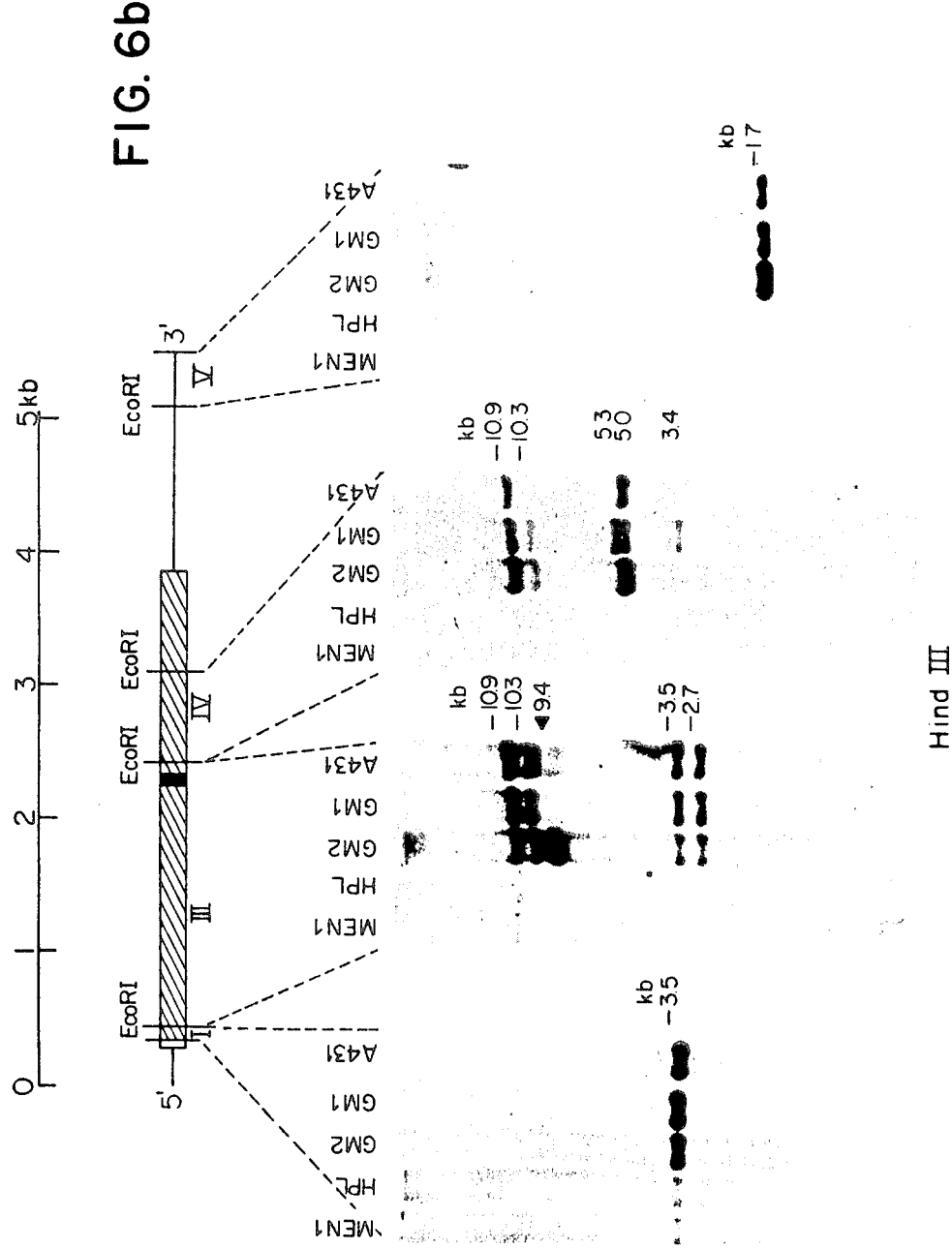

FIGS. 6a and 6b depict the Southern Blot analysis of EGF receptor sequences in various human brain tumours, A431 cells, and human placenta. 15 μg of high molecular weight DNA of A431 cells (A431), human placenta (HPL), glibolastomas (GM1, GM2), and meningioma (MEN1) was digested with EcoRI (a) or HindIII (b). In order to exclude technical artifacts due to incomplete digestions the digestions were repeated several times with large excess of restriction enzymes, revealing the same results. The DNAs were electrophoresed and blotted as described above in part B. The blots were hydbridised to the nick-translated EGF receptor specific cDNA inserts isolated from the cDNA clones depicted in FIG. 7 and FIG. 6 under high stringency conditions as described for part B above. The same blots were reutilised for the diffent probes without detectable loss of signal. For denaturation of the cDNA-genomic DNA hybrids for reutilisation, filters were soaked with slight agitation in 0.5M NaOH, 1.5M NaCl for 10 minutes at room temperature, rinsed with water, neutralised for 2×10 minutes in 0.5M Tris-HCl pH 7.0, 1.5M NaCl and washed in 3×SSC. Filters were kept wet in Saran wrap, preincubated in hybridisation buffer and reused as described above. Dashed lines in the figure indicate the regions of the schematically depicted cDNA giving rise to the hybridisation patterns shown (see also FIG. 7). Arrowheads indicate the location of DNA fragments in the amplified EGF receptor gene of the glioblastoma tumours, but undetectable in other DNAs. Roman numerals denote cDNA fragments used as hybridisation probes (I=p64.4; II=p8.4; III=64.3; V=p62.3).

Northern blot analysis of mRNa from A431 cells, human placenta, and glioblastoma was conducted as follows. A431 cells were grown in Dulbecco's modified Eagle's medium containing 10% foetal calf serum in an atmosphere of 5% CO$_2$-95% air at 37° C. RNA was isolated from frozen tissue of human pacenta, and glioblastoma GM1 after pulverisation in liquid N$_2$ and from fresh A431 cells with the guanidine thiocyanate/cesium chloride method as described (Maniatis, op. cit.). Aliquots (10 microgram) of poly(A) selected mRNA were heated at 60° C. for 10 minutes in a solution containing 50% formamide, 6% formaldehyde and running buffer (20 mM MOPS pH 7.0, 5 mM NaAc, 1 mM EDTA). The samples were electrophoresed at 100 V for 4 hours in 1% agarose gels containing 6% formaldehyde and 1× running buffer. The RNA was transferred with 10×SSC to nitrocellulose filters, fixed by heating at 80° C. for 2 hours and hybridised at 42° C. for 2 days with 2×10$^6$ c.p.m./ml of nick-translated p64.3 probe in a solution containing 50% formamide, 5×SSC, 10% dextran sulphate, 1×Denhardt's mixture, 10 mM sodium phosphate pH 6.8 and 100 microgram/ml salmon sperm DNA. After washing at 65° C. with 0.1×SSC, 0.1% SDS, the filters were autoradiographed for 2 days at −70° C. using intensifier screens. The results are shown in FIG. 8. A unique 38 kb mRNA species not seen in the A431 cells or normal placental cells is indicated by the arrow. This species appears to encode the external domain and at least part of the cytoplasmic domain of the EGF receptor.

REFERENCES

1. Guroff, G. (Ed.) Growth and Maturation Factors (Wiley, New York, 1983).
2. Cohen, S. J. Biol. Chem. 237, 1555–1562 (1962)
3. Ross, R. in Tissue Growth Factors (ed. Baserga, R.) 133–159 (Springer-Verlag, Berlin, 1981).
4. Rozengurt, E. Mol. Biol. Med. (in the press).
5. James, R. & Bradshaw, R. A. Ann. Rev. Biochem. (in the press).
6. Sporn, M. B., & Todaro, G. J. New Eng. J. Med. 303, 878–880, (1980).
7. Waterfield, M. D., Scrace, G. T., Whittle, N., Stroobant, p., Johnsson, A., Wasteson, A., Westermark, B., Heldin, C-H., Huang, J. S. & Deuel, T. F. Nature 304, 34–39 (1983).
8. Doolittle, R. F., Hunkapiller, M. W., Hood, L. E., Devare, S. G., Robbins, K. C., Aaronson, S. A. & Antoniades, H. N. Science 221, 275–277 (1983).
9. Robbins, K. C. Antoniades, H. N., Devare, S. G. Hunkapiller, M. W. & Aaronson, S. A. Nature 305, 605–608 (1983).
10. Deuel, T. F., Huang, J. S. Huang, S. S., Stroobant, P. & Waterfield, M. D. Science 221, 1348–1350 (1983).
11. Dulak, N. C. & Temin, H. M. J. Cell Physiol 81, 161–170 (1973).
12. De Larco, J. E. & Todaro, G. J. Nature 272, 356–358 (1978).
13. Burk, R. R. Expl. Cell. Res. 101, 193–298 (1976).
14. Bourne, H. & Rozengurt, E. Proc. natn. Acad. Sci. U.S.A. 73, 4555–4559 (1976).
15. De Larco, J. E. & Todaro, G. J. Proc. natn. Acad. Sci. U.S.A. 75, 4001–4005 (1978).
16. Roberts, A. B., Frolik, C. A., Anzano, M. A. & Spron, M. B. Fed. Proc. 42, 2621–2626 (1983).
17. Ozanne, B., Fulton, R.J. & Kaplan, P.L.J. Cell Physiol. 105, 163–180 (1980).
18. Kaplan, P. L., Anderson, M & Ozanne, B. Proc. natn. Acad. Sci. U.S.A. 79, 485–489 (1982).
19. Kaplan, P. L. & Ozanne, B. Cell 33, 931–938 (1983).
20. Marquardt, H., Hunkapiller, M. W., Hood, L. E., Twardzik, D. R., De Larco, J. E., Stephenson, J. R. & Todaro, G. J. Proc. natn. Acad. Sci. U.S.A. 80, 4684–4688 (1983).
21. Bowen-Pope, D. F., Di Corletto, P. E. & Ross, R. J. Cell Biol. 96, 679–683 (1983).
22. Collins, M. K. L., Sinnett-Smith, J. W. & Rozengurt, E. J. Biol. Chem. 258, 11689–11693 (1983).
23. Marquardt, H. & Todaro, G. J. J. Biol. Chem. 257, 5220–5225 (1982).

24. Carpenter, G., Stoscheck, C. M., Preston, Y. A. & De Larco, J. E. Proc. natn. Acad. Sci. U.S.A. 80, 5627–5630 (1983).
25. Cohen, S., Ushiro, H., Stoscheck, C. & Chinkers, M. J. Biol. Chem. 257, 1523–1531 (1982).
26. Buhrow, S. A., Cohen, S. & Staros, J. V. J. Biol. Chem. 257, 4019–4022 (1982).
27. Cohen, S., Fava, R. A. & Sawyer, S. T. Proc. natn. Acad. Sci. U.S.A. 79, 6237–6241 (1982).
28. Buhrow, S. A., Cohen, S., Garbers, D. L. & Staros, J. V. J. Biol. Chem. 258, 7824–7827 (1983).
29. Bishop, J. M., Ann. Rev. Biochem. 52, 301–354 (1983).
30. Yamamoto, T., Nishida, T., Miyajima, N., Kawai, S. Ooi, T. & Toyoshima, K. Cell 35, 71–78 (1983).
31. Adamson, E. D. & Rees, A. R. Mol. Cell Biochem. 34, 129–152 (1981).
32. Linsley, P. S., Das, M. & Fox, C. F. in Membrane Receptors (ed. Jacobs, S. & Cuatrecasas, P.) (Chapman & Hall, London and New York) vol. B11, pp 87–113 (1981).
33. Schreiber, A. B., Lax, I., Yarden, Y., Eshhar, Z. & Schelessinger, J. Proc. natn. Acad. Sci. U.S.A. 78, 7535–7539 (1981).
34. Waterfield, M. D., Mayes, E. L. V., Stroobant, P., Bennett, P. L. P., Young, S., Goodfellow, P. N., Banting, G. S. & Ozanne, B. J. Cell Biochem. 20, 149–161 (1982).
35. Kawamoto, T., Sato, J. D., Le, A., Polikoff, J., Sato, G. H. & Mendelsohn, J. Proc. natn. Acad. Sci. U.S.A. 80, 1337–1341 (1983).
36. Richert, N. D., Willingham, M. C. & Pastan, I. J. Biol. Chem. 258, 8902–8907 (1983).
37. Gregoriou, M. & Rees, A. R. Cell Biol. Int. Reports 7, 539–540 (1983).
38. Schelessinger, J., Lax, I., Yarden, Y., Kanety, H. & Libermann, T. A. in Receptors and recognition: antibodies against receptors (ed. Greaves M. F.) (Chapman & Hall, London) (1985).
39. Fabricant, R. N., De Larco, J. E. & Todaro, G. J. Proc. natn. Acad. Sci. U.S.A. 74, 565–569 (1977).
40. Wrann, M. M. & Fox, C. F. J. Biol. Chem. 254, 8083–8086 (1979).
41. O'Keefe, E., Hollenberg, M. D. & Cuatrecasas, P. Arch. Biochem. Biophys. 164, 518–526 (1974).
42. Gullick, W., Downward, D. J. H. Marsden, J. J. & Waterfield, M. D. Analyt. Biochem. (in the press).
43. Ui, N. Analyt. Biochem. 97, 65–71 (1979).
44. Skehel, J. J. & Waterfield, M. D. Proc. natn. Acad. Sci. 72, 93–97 (1975).
45. Waterfield, M. D. & Scrace, G. T. in Biological/Biomedical Applications of Liquid Chromatography (ed. Hawk G. L.) (Marcel Dekker, New York) vol. 18, pp 135–157 (1981).
46. Bennett, H. P. J., Browne, C. A. & Solomon, S. J. Liquid Chromatogr. 3, 1353–1365 (1980).
47. Hewick, R. M., Hunkapiller, M. W., Hood, L. E. & Dreyer W. J. J. Biol. Chem. 256, 7990–7997 (1981).
48. Waterfield, M. D., Scrace, G. & Totty, N. in Practical Protein Biochemistry (Eds. Darbre, A. & Waterfield, M. D.) (Wiley, New York) (in the press).
49. Wilbur, W. J. & Lipmann, D. J. Proc. natn. Aca. Sci. U.S.A. 80, 726–730 (1983).
50. Mayes, E. L. V. & Waterfield, M. D. EMBO J. (in the press).
51. Vennström, B. & Bishop, J. M. Cell 28, 135–143 (1983).
52. Kitamura, N., Kitamura, A., Toyoshima, K., Hirayama, Y. & Yoshida, M. Nature 297, 205–208 (1982).
53. Goodfellow, P. N., Banting, G., Waterfield, M. D., Ozanne, B. Cytogenet. Cell. Genet. 32, 282 (1982).
54. Shimizu, N., Behzadian, M. A. & Shimizu, Y. Proc. natn. Acad. Sci. U.S.A. 77, 3600–3604 (1980).
55. Kondo, I. & Shimizu, N. Cytogenet. Cell. Genet., 35, 9–14 (1983).
56. Spurr, N., Solomon, E., Jannsson, M. Sheer, D., Goodfellow, P. N., Bodmer, W. F. & Vennstrom, B. EMBO J. 3, 159–163 (1984).
57. Greenberg, M. E. % Edelman, G. M. Cell 33, 767–779 (1983).
58. Groffen, J., Heisterkamp, N., Reynolds, F. H. Jr., & Stephenson, J. R. Nature 304, 167–169 (1983).
59. Hayman, M. J., Ramsay, G. M., Savin, K., Kitchener, G., Graf, T. & Beug, H. Cell 32, 579–588 (1983).
60. Privalsky, M. L., Sealy, L., Bishop, J. M., McGrath, J. P. & Levinson, A. D. Cell 32, 1257–1267 (1983).
61. Beug, H., Palmieri, S., Freudenstein, C., Zentgraf, H. & Graf, T. Cell 28, 907–919 (1982).
62. Graf, T. & Beug, H. Cell 34, 7–9 (1983).
63. Frykberg, L., Palmieri, S., Beug, H., Graf, T., Hayman, M. J. & Vennstrom, B. Cell 32, 227–238 (1983).
64. Fung, Y-K. T., Lewis, W. G., Crittenden, L. B. & Kung, H-J. Cell 33, 357–368 (1983).
65. Rabbitts, T. H., Forster, R. A., Baer, R. & Hamlyn, P. H. Nature 306, 806–809 (1983).
66. Rabbitts, T. H., Hamlyn, P. H. & Baer, R. Nature 306, 760–765 (1983).
67. Gelmann, E. P., Psallido Poulos, M. C., Papas, T. S. & Favera, R. D. Nature 306, 799–803 (1983).
68. Roy-Burman, P., Devi, B. G., Parker, J. W. Int. J. Cancer 32, 185–191 (1983).
69. Reddy, E. P., Smith, M. J. & Srinivasan, A. Proc. natn. Acad. Sci. U.S.A. 80, 3623–3627 (1983).
70. Bradford, M. M. Analyt. Biochem. 72, 248–254 (1976).
71. Smith, C. M., Nelson, D. M., King, B. F., Donahue, T. M., Ruzycki, S. M. & Kelley, L. K. Am. J. Obstet. Gynecol. 128, 190–196 (1977).
72. Laemmli, U. K. Nature 227, 680–685 (1970).
73. Schwartz, D., Tizzard, R. & Gilbert, W. Cell 32, 853–869 (1983).
74. Smart, J. E., Opperman, H., Czernilofsky, A. P., Purchio, A. F., Erikson, R. L. & Bishop, J. M. Proc. natn. Acad. Sci. U.S.A. 78, 6013–6017 (1981).
75. Orr, H. T., Lancel, D., Robb, R., Lopez de Castro, J. A. & Strominger, J. L. Nature 282, 266–270 (1979).
76. Ullrich, A. Coussens, L, Hayflick, J. S., Dull, T. J., Gray, A, Tam, A. W., Lee, J, Yarden, Y, Libermann, T. A, Schelessinger J, Downward, J., Mayes, E. L. V., Whittle, N., Waterfield, M. D., Seeburg, P. H., Nature 309, 418–425 (1984).

All the above citations are expressly incorporated by reference.

We claim:

1. A method of diagnosis for the detection of abnormalities in mammalian cell growth comprising obtaining a test sample from a human and assaying the sample of a truncated epidermal growth factor receptor having at least a portion of its mature amino terminus deleted, and correlating detection of said truncated growth factor receptor with abnormal growth control in mammalian cells.

2. A method according to claim 1 wherein the portion of the amino terminus which was deleted contained the receptor's growth factor binding domain.

3. A method according to claim 1 wherein the test sample is body fluid, tissue sample or cultured tumour explant cells.

4. A method according to claim 1 wherein the truncated growth factor receptor exhibits protein phosphokinase activity which is unregulated by its growth factor.

5. A method according to claim 1 wherein the test sample is assayed by immobilising a substance capable of specifically binding to the growth factor receptor's growth factor binding domain or its adjacent regions, contacting the test sample with the immobilised substance under conditions permitting adsorption from the test sample of growth factor receptor, separating the unadsorbed test sample and thereafter determining the truncated growth factor receptor remaining in the test sample.

6. A method according to claim 8 wherein the binding domain and its flanking regions are the first about 500 amino acid residues of the mature receptor.

7. A method according to claim 8 or 9 wherein the substance is a growth factor, an antibody capable of binding to the growth factor binding domain of the growth factor receptor, or an antibody capable of binding the growth factor when the growth factor is bound to the receptor.

8. A method according to claim 1 wherein the test sample is blood serum.

* * * * *